United States Patent [19]
Busch et al.

[11] Patent Number: 5,696,378
[45] Date of Patent: Dec. 9, 1997

[54] HIGH ACCURACY DETERMINATION OF CHLORINE CONTENT BY ISOTOPE DILUTION FLAME INFRARED EMISSION SPECTROMETRY (ID-FIRE)

[75] Inventors: Kenneth W. Busch; Arvie J. Kuehn; Marianna A. Busch, all of Waco, Tex.

[73] Assignee: Baylor University, Waco, Tex.

[21] Appl. No.: 618,758

[22] Filed: Mar. 20, 1996

[51] Int. Cl.⁶ .......................... G01N 21/72; G01N 21/35
[52] U.S. Cl. ................... 250/339.12; 250/339.08; 250/339.13; 250/341.6
[58] Field of Search .......... 250/339.13, 339.12, 250/339.08, 341.6

[56] References Cited

U.S. PATENT DOCUMENTS

| | | | |
|---|---|---|---|
| 5,445,964 | 8/1995 | Lee et al. | 436/60 |
| 5,473,162 | 12/1995 | Busch et al. | 250/341.6 |
| 5,543,621 | 8/1996 | Sauke et al. | 250/339.03 |

*Primary Examiner*—Constantine Hannaher
*Attorney, Agent, or Firm*—Arnold, White & Durkee

[57] ABSTRACT

A method and apparatus for quantitatively determining chlorine content and fractional abundance of chlorine isotopes in unknown samples. When using this method and apparatus to determine chlorine content, isotope dilution principles may be employed. Chlorine isotopes used for diluting an unknown sample may be $^{35}Cl$ or $^{37}Cl$, and relative isotope content in the diluted mixture may be measured using infrared spectrometry.

38 Claims, 18 Drawing Sheets

5,696,378

HIGH ACCURACY DETERMINATION OF CHLORINE CONTENT BY ISOTOPE DILUTION FLAME INFRARED EMISSION SPECTROMETRY (ID-FIRE)

BACKGROUND OF THE INVENTION

1. Technical Field

This invention relates to infrared detection means and methods for detecting and distinguishing selected chlorine isotopes for the purpose of calculating chlorine content present in gaseous samples or in samples which can be converted to a gas phase. The invention is particularly applicable to the fields of water analysis, environmental analysis, chlorofluorocarbon analysis, clinical analysis (such as of blood serum) and process analysis.

2. Description of Related Art

The element chlorine is widely distributed in nature as a mixture of the stable isotopes $^{35}Cl$ and $^{37}Cl$. In its naturally occurring isotopic form, chlorine is about 75.77% $^{35}Cl$ and about 24.23% $^{37}Cl$. Chlorine is also used extensively in its various oxidation states. Aqueous elemental chlorine ($Cl_2$) and hypochlorite ($OCl^-$), for example, are employed as bleaching agents and as disinfectants to prevent the spread of waterborne diseases. Because of the reactivity of the higher oxidation states of chlorine, the element occurs in nature primarily as the chloride ion (Cl) and is one of the major inorganic constituents of surface waters, groundwaters, and wastewaters. In seawaters, chloride levels, expressed as chlorinity, are approximately related to salinity and can be used to determine the concentrations of all other bio-unlimited elements present in a sample. Chloride content is also used as an indicator of water condition. For example, elevated chloride concentrations in the sewerage of coastal areas may signal seawater intrusion into the system, while in potable water they are often associated with waste water contamination. In process waters, chloride concentrations are monitored regularly since elevated levels are generally associated with increased deterioration of metallic pipes and structures, while in cooling water, they are used to indicate the cycles of concentration. Chloride content can also be used to identify unknown sources of water, such as aquifers, wells, outcrops or springs. In other cases chloride content can be used to detect the presence of environmental pollution in surface waters such as lakes, ponds, streams, creeks, or in storm water runoff. Chloride content can also be monitored in industrial process effluents to ensure compliance with environmental laws.

Because of the widespread use and occurrence of the many forms of chlorine, analytical methods for their determination are of great importance. A large number of methods exist for the determination of chloride ion and chlorine in aqueous samples. These include chromatographic, spectrometric, potentiometric and titrimetric procedures, with the most widely used methods involving titration of the sample.

For the titrimetric determination of aqueous chloride, various argentometric methods exist which use either indicators or potentiometers to detect the endpoint. Alternatively, mercuric nitrate can be used to titrate chloride ion using diphenylcarbazone as an indicator.

For the determination of chlorine in bleach bath liquors and natural and treated waters in concentrations greater than about 1 mg/L, iodometric titration is the method of choice. For chlorine levels less than this amount, amperometric titrations are preferred, but require greater operator skill to avoid loss of chlorine through mechanical stirring. Poor endpoints are also a problem unless the electrodes are properly cleaned and conditioned. Alternatively, N,N-diethyl-p-phenylenediamine (DPD) can be used to determine dissolved chlorine colorimetrically or titrimetrically, using ferrous ammonium sulfate.

All of these titrimetric methods may be subject to interference by a variety of species including, bromide, iodide, cyanide, sulfide, and orthophosphate (for chloride) and other oxidizing agents (for chlorine). Because of the problems associated with existing procedures, new analytical methods for the determination of chloride ion and chlorine in aqueous samples are of great importance.

In addition to problems inherent with titrimetric methods, most instrumental methods of analysis require some form of prior calibration in order to provide quantitative information on a constituent in a sample such as chlorine. This calibration procedure is crucial to the accuracy of the analysis since virtually all analytical methods are affected to a greater or lesser extent by the presence of other constituents in the sample matrix. The presence of these other constituents in the sample degrades the accuracy of the analysis and leads to what is commonly referred to in analytical chemistry as an interference. Since virtually all instrumental methods suffer from matrix interferences, the accuracy obtained in a determination that relies on prior instrument calibration depends on how closely the calibration standards used to prepare the calibration curve match the composition of the sample being analyzed. The preparation of complex calibration standards not only requires a prior knowledge of sample composition, which may or may not be available for a given sample, but also requires additional time and effort.

Determinations based on isotope dilution avoid the use of calibration curves altogether and are inherently accurate as long as the isotopes of the given element behave identically in the chemical processes involved in the analysis, which is the case for virtually all common chemical processes. Isotope dilution experiments typically involve either radioactive isotopes, which can be detected by standard radiochemical techniques, or mass spectrometric determination, if stable isotopes are used. In general, the expense involved with the disposal of radioactive wastes today has made the use of radioactive isotope dilution less attractive. By contrast, mass spectrometric methods of analysis often require extensive sample preparation prior to the actual mass spectrometric measurement so that only eight samples may be analyzed per day. See Encyclopedia of Analytical Science (1995).

As an alternative to more costly and time consuming methods, combustion flames have long been employed analytically as spectroscopic sources. Although the analytical application of combustion flames as spectroscopic sources has been studied in great depth, until recently the work has been confined almost entirely to studies of the radiant emissions falling within the UV-visible region of the electromagnetic spectrum. See Mavrodineanu and Boiteux (1965).

Recently, analytical use of combustion flame infrared spectrometry has been explored. U.S. Pat. No. 5,246,868 describes an apparatus and method for qualitatively and quantitatively analyzing infrared emission from excited molecules in samples of interest. In particular, this reference discloses that particular molecular components in a gaseous sample may be excited to emit infrared radiation at characteristic wavelengths and in proportion to the quantity of the component in the sample. The detection of particular components such as $CO_2$ and HCl are described. Using the method and apparatus of this patent, a gaseous sample containing an infrared measurable component or a gas derived from a nongaseous sample containing an infrared measurable component is excited using heat from a flame so as to emit infrared radiation at the characteristic wavelength and with an intensity proportional to the quantity of the infrared measurable component in the sample. Infrared radiation is detected at the characteristic wavelength by a spectrometer capable of performing a Fourier-transform analysis to produce a spectrical analysis characteristic of the sample. The method of U.S. Pat. No. 5,246,868 is directed toward applications such as detecting carbon-oxide impurities in process gas, carbonate or organic impurities in water, $CO_2$ content in carbonated beverages, chloride ion concentration and the detection of other compounds such as silicon, sulfur and fluorine containing compounds. Although the apparatus and method of U.S. Pat. No. 5,246,868 represent an improvement over the prior art in determining concentrations of selected components present in a sample, the accuracy of quantitative determination using this method is dependent upon proper calibration procedures. As with other methods of the prior art, these calibration procedures can be quite complex and time consuming when analyzing samples including constituents that cause matrix interference. As an additional inconvenience for chloride ion determinations, the method of U.S. Pat. 5,246,868 relies on chemical oxidation (in the case of $Cl^-$) or acidification (in the case of $Cl_2$) to convert chloride ions or dissolved $Cl_2$ in solution to gaseous $Cl_2$ for analysis.

SUMMARY OF THE INVENTION

Figure 1:
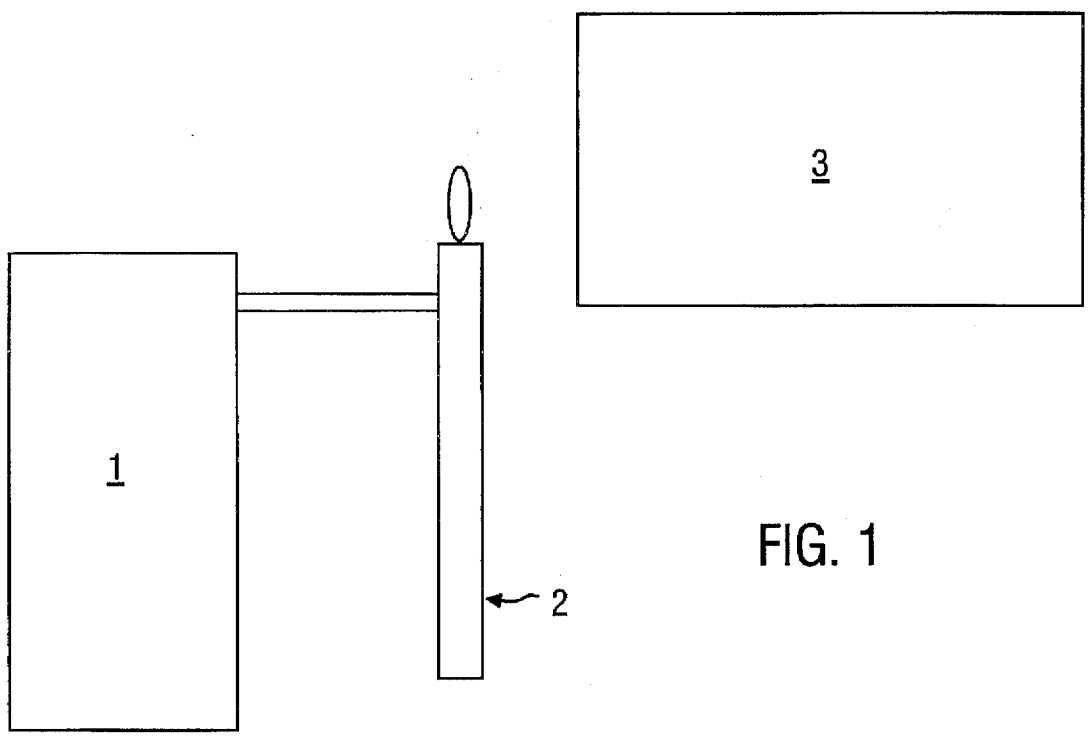
FIG. 1 is a simplified schematic diagram of one embodiment of a chlorine isotope dilution flame infrared emission spectrometry (ID-FIRE) system for analyzing aqueous chloride ion solutions.

As used herein, "chlorine" is meant to refer to chlorine atoms, whether present alone as chloride ions, existing in diatomic form as chlorine gas or attached to atoms of other elements such as carbon.

It is now been discovered that chlorine isotopes can be detected and distinguished based on their characteristic infrared emission wavelengths. It is also been discovered that the ability to distinguish the infrared emissions of the chlorine isotopes will allow chlorine content to be determined based on isotope dilution techniques now only possible using radioactive isotopes or mass spectrometric methods of analysis. Surprisingly, by taking advantage of the distinct infrared emission wavelengths of different chlorine isotopes, quantitative determinations using isotope dilutions have been greatly simplified. Using this principle, this invention provides a method of detecting and quantitatively determining the content of selected components such as chlorine that is simple, rapid and inexpensive. In addition, this invention provides an easy and efficient method of converting chloride ions into $Cl_2$ for analysis. Therefore, the method of this invention offers benefits to the public, including lowered production costs and the ability to conduct more extensive monitoring of drinking water and waste water effluents. Accordingly, the present invention provides a solution to one or more of the disadvantages previously described or otherwise known to one skilled in the art.

In one broad respect, this invention is a method of quantitatively determining chlorine content of a first sample, the method comprising combining said first sample with a second sample containing chlorine isotopically enriched with either a $^{35}Cl$ or $^{37}Cl$ isotope to form a mixture, and exciting said mixture such that the mixture emits an infrared spectrum, and wherein the chlorine content of the first sample is quantitatively determined from the infrared emissions of the mixture.

In another respect, this invention is a method of quantitatively determining chlorine content of a sample, comprising the steps of mixing a first sample containing an unknown content of chlorine in its naturally occurring isotopic form with a second sample containing a known content of chlorine isotopically enriched with a chosen chlorine isotope, so as to form a mixture, converting at least a portion of the chlorine in said mixture to vibrationally excited HCl, said HCl emitting a ro-vibrational infrared spectrum, and measuring infrared emissions from said vibrationally excited HCl, wherein the chlorine content of the first sample is quantitatively determined by comparing the HCl infrared emissions of the chosen chlorine isotope with the HCl infrared emissions of the other chlorine isotope present in said vibrationally excited HCl.

In another respect, this invention is a method useful for quantitatively determining the chloride ion content of a solution, comprising the steps of mixing a first aqueous sample containing an unknown content of chloride ion in its naturally occurring isotopic form with a second aqueous sample containing a known content of chloride ion isotopically enriched with a chosen chlorine isotope, so as to form a mixture of chloride ions, subjecting said mixture of chloride ions to electrolysis under conditions effective to convert at least a portion of the chloride ions to $Cl_2$, reacting said $Cl_2$ with hydrogen under conditions effective to convert at least a portion to HCl, heating said HCl to convert at least a portion to a vibrationally excited state, said HCl emitting a ro-vibrational infrared spectrum, and measuring infrared emissions from said vibrationally excited HCl, wherein the chloride ion content of the first sample is quantitatively determined by comparing the HCl infrared emissions of the chosen chlorine isotope with the HCl infrared emissions of the other chlorine isotope present in said vibrationally excited HCl.

In another respect, this invention is an apparatus useful for quantitatively determining fractional abundance of chlorine isotopes or chloride ion content in a solution using time infrared spectrometry, comprising sample introduction means for converting chloride ions into $Cl_2$ having an electrolysis cell for containing aqueous solutions of NaCl; sample excitation means having a burner, wherein $Cl_2$ gas from the sample introduction means issues from the burner in the presence of hydrogen and mixes with air or oxygen so as to fuel a flame, thereby combusting a portion of the hydrogen and $Cl_2$ gases so as to generate vibrationally excited HCl molecules, said HCl molecules emitting infrared radiation at a characteristic wavelength; infrared discriminating detector means having an interferometer and capable of detecting and distinguishing infrared radiation at the characteristic wavelengths of $H^{35}Cl$ and $H^{37}Cl$ and generating an output signal representative thereof; and computation means capable of performing signal processing on the output signal generated by the discriminating detector means so as to provide an output indicative of the relative quantities of $H^{35}Cl$ and $H^{37}Cl$ present in the HCl.

In another respect, this invention is a method useful for quantitatively determining fractional abundance of chlorine isotopes present in a sample, comprising the steps of exciting at least a portion of the sample, said portion of the sample emitting a distinctive and characteristic infrared spectra, and measuring infrared emissions from said excited portion of the sample, wherein the fractional abundance of chlorine isotopes present in the sample is quantitatively determined from the infrared emissions of the portion of the sample.

Because interferences are virtually impossible, the method of the present invention can be used to verify the results obtained with other methods of analysis, such as ion selective electrodes or argentometric titrations. Since the method is free of bias, the reliability of the results is only limited by the precision of the method. The precision of the method can be increased to the desired level in several ways: (1) the sample size can be increased so that more than 50 scans can be accumulated; (2) several sample aliquots can be run by the method and the results averaged; (3) a number of rotational lines can be measured with a single run of sample and the results averaged; (4) a combination of the above can be used.

Thus, the discovery of the surprising fact that infrared spectrometry may be used to determine unknown chlorine content allows analyses which have all the advantages of isotope dilution methods, including inherent accuracy, without the time and effort of preparing calibration curves. At the same time, the method of the present invention offers significant advantages over standard isotope dilution methods, including no expense for the disposal of radioactive wastes, no extensive sample preparation and an ease of operation allowing many samples to be analyzed in a typical day.

DETAILED DESCRIPTION OF THE PREFERRED EMBODIMENTS

The present invention relates to a simple, rapid method of chloride ion analysis in aqueous samples based on stable isotope dilution where the isotopic composition of the sample is determined by flame infrared emission (ID-FIRE) spectrometry. In particular embodiments, the method uses the isotopic shift in the HCl stretching vibration observed by means of high resolution Fourier-transform infrared spectrometry. Because the method involves the measurement of isotopic ratios as obtained by spectrometric line intensities, it is essentially free of chemical interferences and can serve as a reference method for chloride ion analysis.

Given the fact that the combustion of chlorine-containing compounds in a flame produces HCl, infrared emission detection under high resolution conditions provides spectra wherein the P and R branches of the HCl infrared emission can be easily detected above the flame background in the region from about 3200–2400 $cm^{-1}$. Since the HCl emission band lies between the water emission band at about 3800–3200 $cm^{-1}$ and the carbon dioxide emission band centered at about 2262 $cm^{-1}$, the strong, well-resolved infrared emission from HCl should also be useful analytically for the determination of Cl in a variety of chlorine-containing samples (Kubala et al., 1989b).

In the practice of this invention, the chlorine content present in a sample may be quantitatively determined by taking advantage of the mass dependence of the rotational constants between the infrared emission spectrum of $H^{35}Cl$ and $H^{37}Cl$. This mass dependence of the rotational constants produces a spectral shift that makes it possible to make quantitative determinations of chlorine concentration using isotope dilution principles without the expense and complications associated with isotope dilution methods employing radioactive isotopes or mass spectrometry.

In general, the method of the present invention is practiced by mixing a first sample containing an unknown content of chlorine in its naturally occurring isotopic form with a second sample containing a known content of chlorine that has been isotopically enriched with a chosen chlorine isotope that is either $^{35}Cl$ or $^{37}Cl$. Although the use of $^{36}Cl$ in the method of this invention is not discussed here due to its radioactive nature, it should be understood that the method of this invention may be successfully practiced using a mixture of chlorine isotopes that contains $^{36}Cl$. In the practice of the present invention, the mixture of the first and second samples may be in many forms, including gaseous or any other form that is capable of being excited.

In the practice the present invention, the chlorine present in the mixture may be converted into HCl using any means capable of doing so, including a combustion flame. The HCl is then vibrationally excited so as to produce a characteristic HCl infrared emission spectrum, either in the same step as the conversion or in a separate excitation step. The infrared emission from the vibrationally excited HCl is then measured by any means capable of distinguishing the infrared emissions of $H^{35}Cl$ from $H^{37}Cl$, such as a Fourier-transform infrared spectrometer (FTIR). The unknown chlorine content of the original first sample can then be quantitatively determined by comparing the relative emissions of these HCl isotopic forms. Advantageously, only a portion of the chlorine present in the mixture of the first and second samples needs to be converted to HCl, and only a portion of the HCl needs to be vibrationally excited. This is true because the method of the present invention relies on the measured ratio of the chlorine isotopes present in the vibrationally excited HCl rather than the absolute quantity of chlorine present.

Analysis of Aqueous Samples

In one embodiment of this invention, the chloride ion concentration present in an aqueous sample is quantitatively determined using an apparatus having a sample introduction means, a sample excitation system, a detecting means and a computation means. The sample introduction means converts at least a portion of aqueous chloride ions into chlorine gas ($Cl_2$), which is in turn sparged from solution and transferred to the sample excitation system. The sample excitation system converts at least a portion of the $Cl_2$ from the sample introduction means into HCl and vibrationally excites a portion of this HCl to emit a characteristic ro-vibrational spectrum consisting of P- and R-branches. The detecting means monitors the P- and R-branches of the HCl stretching vibration and is capable of detecting and distinguishing between the infrared radiation wavelengths produced by different chlorine isotopes, and is further capable of generating an output signal representative thereof for further processing by the computation means. The computation means converts the detecting means output signal into a representation of the HCl infrared spectrum indicative of the relative quantities of $^{35}Cl$ and $^{37}Cl$ present in the vibrationally excited HCl. The computation means may employ any well known device or method capable of processing the output signal from the detection means, including a computer.

In one preferred embodiment of the apparatus of the present invention, the sample introduction system has an electrolysis cell capable of converting aqueous chloride ions to $Cl_2$, and a means for purging the $Cl_2$ from the cell and delivering it through a conduit to a sample excitation means using hydrogen gas. In this embodiment, the sample excitation system includes a two tube concentric burner in which a gaseous mixture of hydrogen and $Cl_2$ produced by the electrolysis cell is mixed and combusted with air in a hydrogen flame of sufficiently high temperature to convert the $Cl_2$ into vibrationally excited HCl emitting a characteristic ro-vibrational HCl spectrum. The HCl ro-vibrational spectrum produced by the vibrationally excited HCl is monitored using a Fourier-transform infrared spectrometer which collects data of sufficiently high resolution (about 0.75 $cm^{-1}$) to clearly resolve $H^{35}Cl$ lines from those emitted by $H^{37}Cl$. Using this high resolution, the apparatus of this embodiment may be practiced in order to take advantage of the isotope shift between the ro-vibrational infrared spectra of $H^{35}Cl$ and $H^{37}Cl$ in order to determine the chloride ion concentration in a solution using principles of isotope dilution.

One preferred embodiment of the apparatus of the present invention consists of three basic components as shown in FIG. 1, which combine to produce the desired result. The sample introduction system 1 converts aqueous chloride ion into chlorine ($Cl_2$), which is sparged from solution and introduced into the sample excitation system 2. The sample excitation system converts the $Cl_2$ gas into HCl and serves to produce vibrationally excited HCl, which emits a characteristic ro-vibrational spectrum consisting of P- and R-branches. The P- and R-branches of the HCl stretching vibration are monitored with an FTIR modified for flame infrared emission measurements 3, which serves as the third component of the invention and separates the spectral components of $H^{35}Cl$ from $H^{37}Cl$.

Sample Introduction Means

Figure 2:
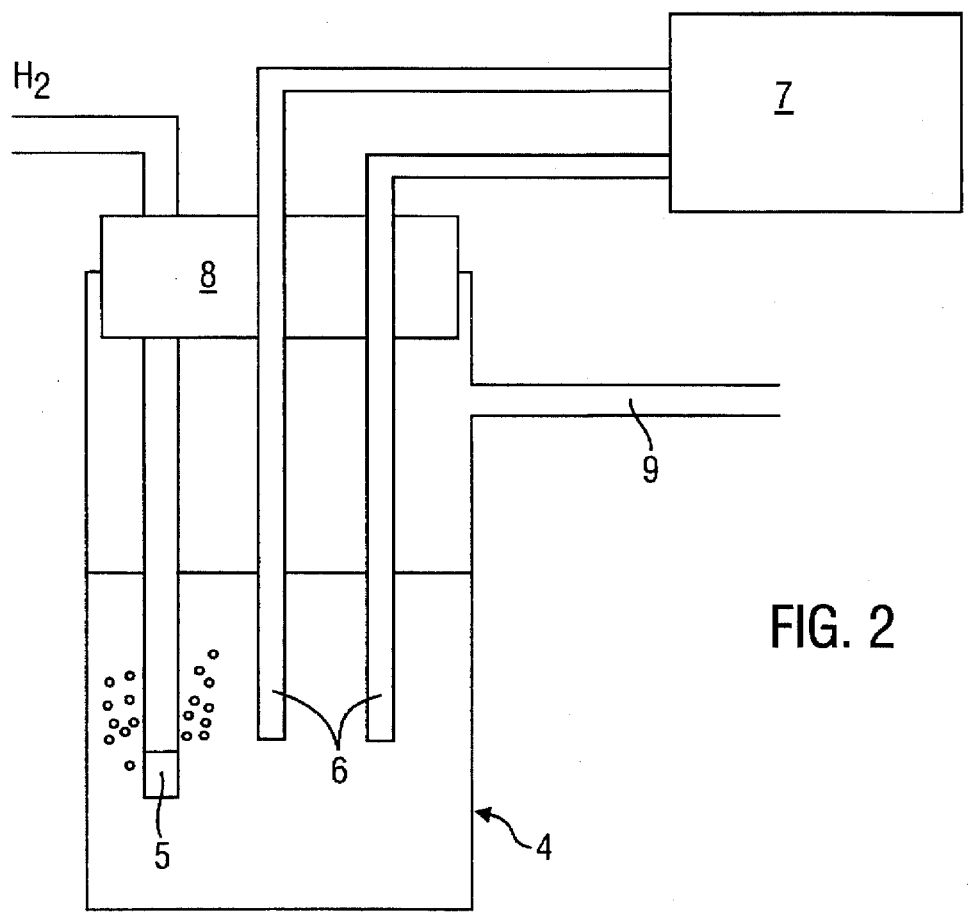
FIG. 2 is a simplified schematic diagram of one embodiment of a sample introduction means for use in the isotope dilution ID-FIRE analysis of aqueous chloride ion solutions.

FIG. 2 shows a schematic diagram of one preferred embodiment of the sample introduction system. An aqueous sample is transferred to a miniature electrolysis cell 4, which can be purged by hydrogen with a porous glass frit 5. A pair of platinum electrodes 6 dip into the cell and are connected to an electrical power supply 7. The top of the cell is sealed with a teflon plug 8 and the gases liberated from the cell are transferred by teflon tubing 9 to the sample excitation system.

Because the method is based on isotopic ratios, it is not important that all the chloride ion in the cell be converted to $Cl_2$ or whether other electrolysis products containing chlorine are produced (such as $ClO_3$). Moreover, because of the specificity of the method, it does not matter whether other constituents such as $Br^-$ or $I^-$ are also electrolyzed to produce $Br_2$ and $I_2$.

Sample Excitation Means

Figure 3:
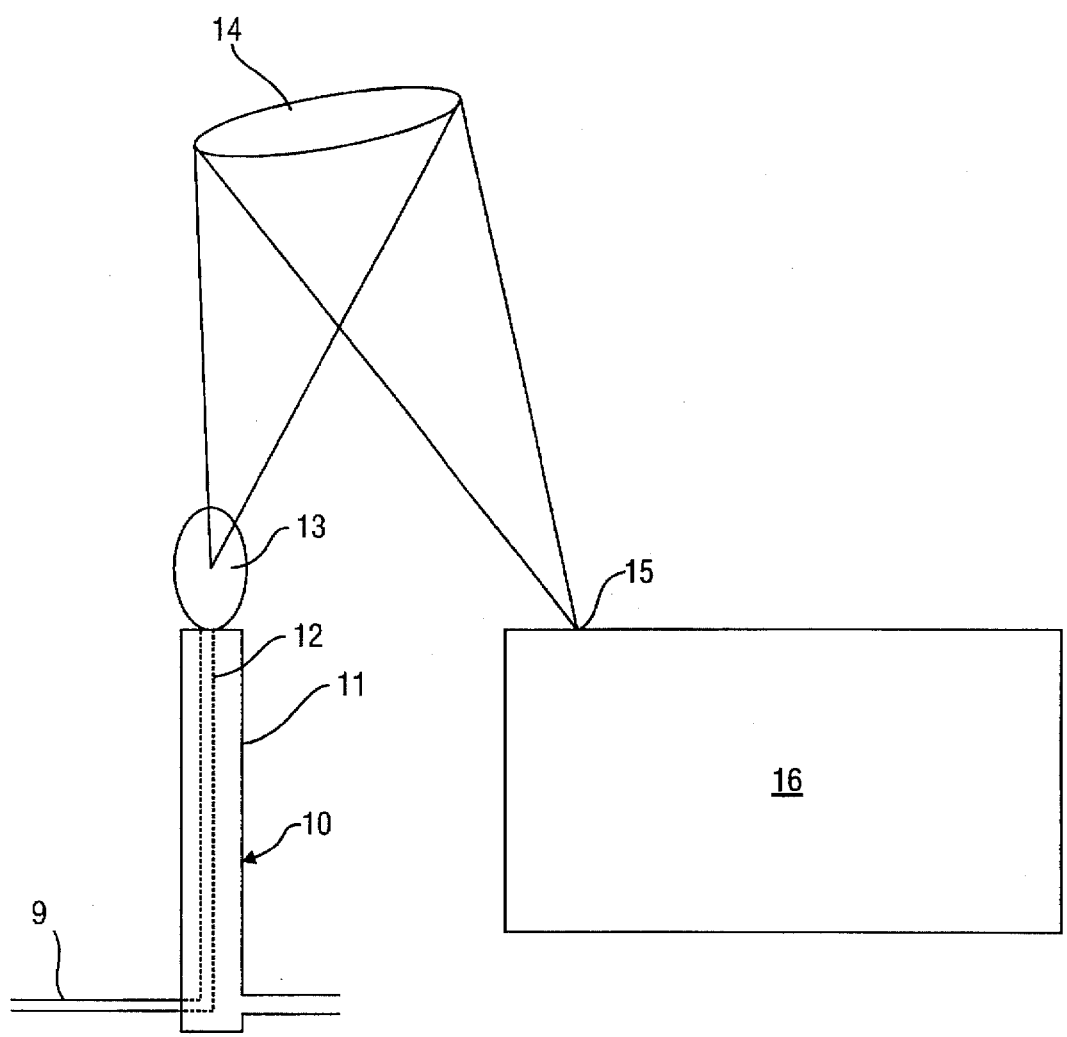
FIG. 3 is a combined simplified diagram of example embodiments of sample excitation means and computation means for use in the isotope dilution ID-FIRE analysis of aqueous chloride ion solutions.

One preferred embodiment of the sample excitation system is shown in FIG. 3. This embodiment consists of a miniature two-tube concentric burner 10, where air issues from the outer tube 11 and hydrogen and $Cl_2$ produced by electrolysis issue from the inner tube 12. In this embodiment, a hydrogen/air diffusion flame 13 is maintained at the tip of the burner. Any $Cl_2$ present in the gases fed to the burner is immediately converted to HCl in the flame. Again, it is important to stress that, because the method is based on isotopic ratios (whatever happens to one isotope also happens in the exact same manner to the other), it is not important that all of the $Cl_2$ be converted into HCl in the flame. At the temperature of the flame (~1200K), a portion of the HCl present in the flame exists in vibrationally excited states which emit the characteristic ro-vibrational spectrum associated with the stretching vibration of HCl.

Specificity is achieved by the combination of electrolysis and flame combustion. Thus, only certain constituents in the sample will produce gaseous electrolysis products that can be transferred to the flame. Of those that are produced (say $Br_2$ or $I_2$), they are either infrared inactive, or produce infrared active combustion products that emit light at a different wavelength from HCl, or simply decompose at the flame temperature.

In this preferred embodiment, the burner is constructed from ceramic tubing to avoid problems with corrosion associated with $Cl_2$. All gas transfer lines are TEFLON (polytetrafluoroethylene) for the same reason.

Although a two-tube concentric burner is employed in this embodiment, it will be understood by those skilled in the art that a variety of other burner configurations may be employed to expose hydrogen and $Cl_2$ from the sample introduction system to a combustion flame, including, for example, a single tube burner. Oxidant for burner combustion may be air, oxygen, other suitable oxidant gases known to those skilled in the art, or mixtures thereof. Oxidant for combustion may be obtained from the atmosphere surrounding a burner or by any other method known to those of skill in the art. When oxidant for combustion is obtained from the atmosphere surrounding a burner it is referred to as being "entrained air". As used herein, the term "hydrogen/air" means a flame fueled by a mixture of hydrogen and air using any method known to those skilled in the art, including for example, where air is supplied to the flame by a separate feed or obtained from the atmosphere surrounding the flame in an entrained air arrangement. The term "hydrogen/oxygen" means a burner flame fueled by a mixture of hydrogen and oxygen using any method known to those skilled in the art.

Detecting and Computation Means

In one preferred embodiment of the detecting and computation means shown in FIG. 3, radiation from the sample excitation flame is collected by a spherical mirror 14 and transmitted to the emission port 15 of a commercial Fourier-transform infrared spectrometer (FTIR) 16. The FTIR collects spectral data from 50 scans the interferometer and processes the data by computer to generate a high resolution spectrum with a resolution of about 0.75 cm$^{-1}$. At this resolution, lines from H$^{35}$Cl are clearly separated from those emitted by H$^{37}$Cl. The number of scans by the inferometer necessary to achieve a strong spectrum may vary with the concentration of the sample. For example, a highly concentrated sample may require fewer scans, while a less concentrated sample may require more. In some embodiments of this invention the number of scans required varies from about 20 to about 50, while in others the number of scans required may lie outside this range. The time required for spectral acquisition and data processing may be about 2.5 minutes.

Although pure hydrogen gas is used as a purging agent in the preceding preferred embodiment, mixtures of hydrogen and other gases, would also be acceptable. In addition, those skilled in the art will recognize that excitation may be accomplished using a variety of different burner configurations, including but not limited to those configurations using hydrogen gas with oxygen or entrained air. In embodiments where entrained air is used, no flow of oxidant is required in a burner outer tube to sustain a flame. It has been found that particularly good results may be achieved in the practice of the present invention using entrained air. Moreover, reaction of hydrogen and Cl$_2$ to produce HCl, followed by another type of excitation means would also be acceptable. Other excitation means that may be employed in the practice of this invention include: 1) other types of thermal excitation, such as a furnace excitation; 2) excitation by electron impact in a gas discharge; and 3) photo-excitation with an appropriate source.

One preferred embodiment of the method of the present invention is practiced by mixing an aqueous first sample containing an unknown concentration of NaCl in its naturally occurring isotopic form with a second aqueous sample containing an unknown concentration of NaCl that has been isotopically enriched with the chosen chlorine isotope $^{37}$Cl. Whatever the chosen isotope, the concentration of chosen isotope as a percentage of total chlorine present in the isotopically enriched second sample may vary, as it may be mathematically accounted for in chlorine determination equations. A concentration of greater than about 50% is preferred, and a concentration of between about 90% and about 100% is most preferred.

In naturally occurring isotopic form, chlorine is present as about 75.77% $^{35}$Cl and about 24.23% $^{37}$Cl. Therefore, in this embodiment the mixture of the first and second samples results in a chloride ion mixture that is made up of greater than about 24.23% $^{37}$Cl. When the mixture of the first and second samples is subjected to electrolysis in the sample introduction means of the present invention, isotopically enriched Cl$_2$ is produced. The isotopically enriched Cl$_2$ is then sparged from solution and purged from the cell with hydrogen gas. The resulting mixture of Cl$_2$ and hydrogen is then combusted in a flame to produce isotopically enriched HCl, with more than about 24.23% of the HCl consisting of H$^{37}$Cl. In this preferred embodiment, the temperature of the flame in the excitation means is sufficiently high so as to simultaneously form and excite the HCl to produce infrared emissions, the minimum temperature for excitation being any temperature above room temperature, preferably above about 600K. The HCl infrared emissions are then detected by the detecting means and a spectral analysis that is characteristic of the relative quantities of chlorine isotopes present in the HCl is generated by the computation means. The chloride ion concentration is then quantitatively determined by comparing the infrared emissions of the H$^{37}$Cl isotope form with that of the H$^{35}$Cl isotope form. If improved accuracy is required, the procedure of this preferred embodiment can be repeated and the results averaged.

Advantageously, the relatively simple method and apparatus of the previous embodiments may be employed to determine chloride ion concentration in solutions ranging from, but not limited to, samples of industrial process water to water samples taken from oceans or aquifers. Drinking water (potable water), cooling water, sewage treatment effluent, environmental samples, industrial process effluent, waste water, sea water, brine samples, ground water, surface water, aqueous bleach samples, or any mixtures thereof may be analyzed using this method. Specific examples include well water, aquifer water, outcrop water, spring water, ocean or sea water, lake water, pond water, stream water, creek water, storm water run off, brine water from wells, or mixtures thereof. The method is simple, free of interferences, rapid (analysis time under three minutes), and does not require any special skills beyond those required in routine analytical chemistry.

Analysis of Non-Aqueous Samples

In addition to measuring chloride ion concentration in aqueous solutions, the principle of isotope flame infrared emission spectrometry can be used to determine chlorine concentrations present in other types of solutions as well. These other types of solutions include gaseous and non-aqueous liquid solutions, including but not limited to, process gases used in manufacturing, electronic-grade gases used in the manufacture of electronic devices, gaseous effluents such as air conditioning waste gas, dry cleaning effluents, and mixtures thereof.

In one embodiment of the present invention, chlorine containing organic liquids may be analyzed using the method of the present invention. In this embodiment, a first organic liquid sample, such as carbon tetrachloride, containing an unknown concentration of chlorine is mixed with an isotopically enriched second organic liquid sample containing a known concentration of chlorine isotopically enriched with a chosen chlorine isotope. For example, the first sample may be mixed with isotopically enriched carbon tetrachloride made in the lab or purchased commercially. This mixture is then aspirated and introduced to a combustion flame, where a portion of the chlorine in the mixture is convened to vibrationally excited HCl, thereby emitting a ro-vibrational infrared spectrum. The HCl infrared emissions are then measured using a means capable of distinguishing the infrared emissions of $H^{35}Cl$ from $H^{37}Cl$. These infrared measurements may then be used to calculate the concentration of chlorine present in the first sample in a manner similar to that employed in the analysis of aqueous samples.

Further details on additional methods, compositions and apparatus that may be employed to generate vibrationally excited HCl from non-aqueous chlorine containing samples in the practice of the present invention may be found in U.S. Pat. No. 5,473,162 to Busch et al. The information contained in this patent, including descriptions of methods, compositions, apparatus and experimental data are hereby incorporated by reference.

Chemical Oxidation to Generate Chlorine Gas From Samples

In addition to electrolysis, many other methods exist for generating $Cl_2$ from chlorine containing samples. These other methods include, but are not limited to, chemical oxidation reactions.

Since chlorine gas reacts rapidly with hydrogen under flame conditions to form HCl $$H_2+Cl_2=2HCl$$

any reaction that generates elemental chlorine in a quantitative manner could serve as the basis of an analytical procedure employing flame infrared emission as a highly specific means of detection. As one example, samples containing dissolved chloride ion could be oxidized to elemental chlorine according to the following half-cell ($E°=-1.36$ V), $$2Cl^-=Cl_2(aq)+2e^-$$

using such strong oxidants as permanganate ion ($E°=+1.51$ V in acid solution), peroxide ion ($E°=+1.77$ V in acid solution) or peroxydisulfate ion ($E°=+2.01$ V). The resulting chlorine gas could then be purged from solution using an inert gas and introduced into a hydrogen-air time to form excited HCl which could be detected by means of its infrared emission.

Another example is the determination of available chlorine in bleaches prepared from elemental chlorine and hypochlorite. In solution these species produce hypochlorous acid ($pK_a=7.60$ at 25° C.) according to the following two equations, respectively, $$Cl_2+2H_2O=HOCl+H_3O^++Cl^-$$

$$OCl^-+H_2O=HOCl+OH^-$$

and the term available chlorine refers to the total oxidizing power of the solution due to chlorine, hypochlorous acid and hypochlorite ion, expressed in terms of an equivalent quantity of $Cl_2$. (The distribution of Cl between these three species is temperature and pH dependent). Since the following equation $$Cl_2+2H_2O=HOCl+H_3O^++Cl^-$$

is readily reversible ($K^{-1}_{eq}=2.2\times10^3$ at 24° C.), addition of acids leads to the rapid generation of dissolved molecular chlorine which can be purged from solution, converted to HCl in the flame, and detected by infrared emission as described previously.

In those embodiments of this invention utilizing chemical oxidation to generate chlorine gas from chlorine-containing samples, it is important that a constant flow system be provided. Such a flow system may feed the chlorine containing sample into the oxidizing medium so that chlorine is produced in a steady and continuous manner, creating a steady emission signal over the time required by the FTIR to scan the spectrum. Alternatively, the oxidizing medium may be fed into the chlorine containing sample, or a feed of the chlorine containing sample and a feed of the oxidizing medium may be combined to produce a steady emission signal.

Further details on additional methods, compositions and apparatus that may be employed to generate $Cl_2$ from chlorine containing samples in the practice of the present invention may be found in U.S. Pat. No. 5,473,162 to Busch et al. The information contained in this patent, including descriptions of methods, compositions, apparatus and experimental data are hereby incorporated by reference.

Non-Combustion Excitation Methods

In addition to flame combustion excitation means, other methods may be employed in the practice of this invention for producing vibrationally excited HCl. These methods include, but are not limited to thermal excitation (such as by furnace), laser excitation, or electrical excitation (such as by plasma). Detailed descriptions of these methods may be found in U.S. Pat. No. 5,473,162 to Busch et al., which is hereby incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

Further details on additional methods, compositions and apparatus that may be employed to produce vibrationally excited HCl in the practice of the present invention may be found in U.S. Pat. No. 5,473,162 to Busch et al. The information contained in this patent, including descriptions of methods, compositions, apparatus and experimental data are hereby incorporated by reference.

EXAMPLES

The following examples are illustrative of the principles and technique of the ID-FIRE method of the present invention. Example 1 illustrates a quantitative determination of chloride ion concentration in a prepared aqueous sample using the ID-FIRE technique of the present invention. Example 2 shows the use of one embodiment of the ID-FIRE technique of this invention to determine the chloride ion concentration in an unknown aqueous sample. Example 3 demonstrates that high resolution HCl infrared spectra can, in principle, be obtained by the aspirated combustion of chlorine containing liquids, such as carbon tetrachloride and trichlorotrifluoroethane.

Example 1—Quantitative Chloride Ion Determination in a Prepared Sample Using $^{37}Cl$ as Chosen Isotope

ID-FIRE Experimental Apparatus

In this example, the apparatus described below was used to quantitatively determine the chloride ion concentration present in a prepared aqueous solution.

Figure 4:
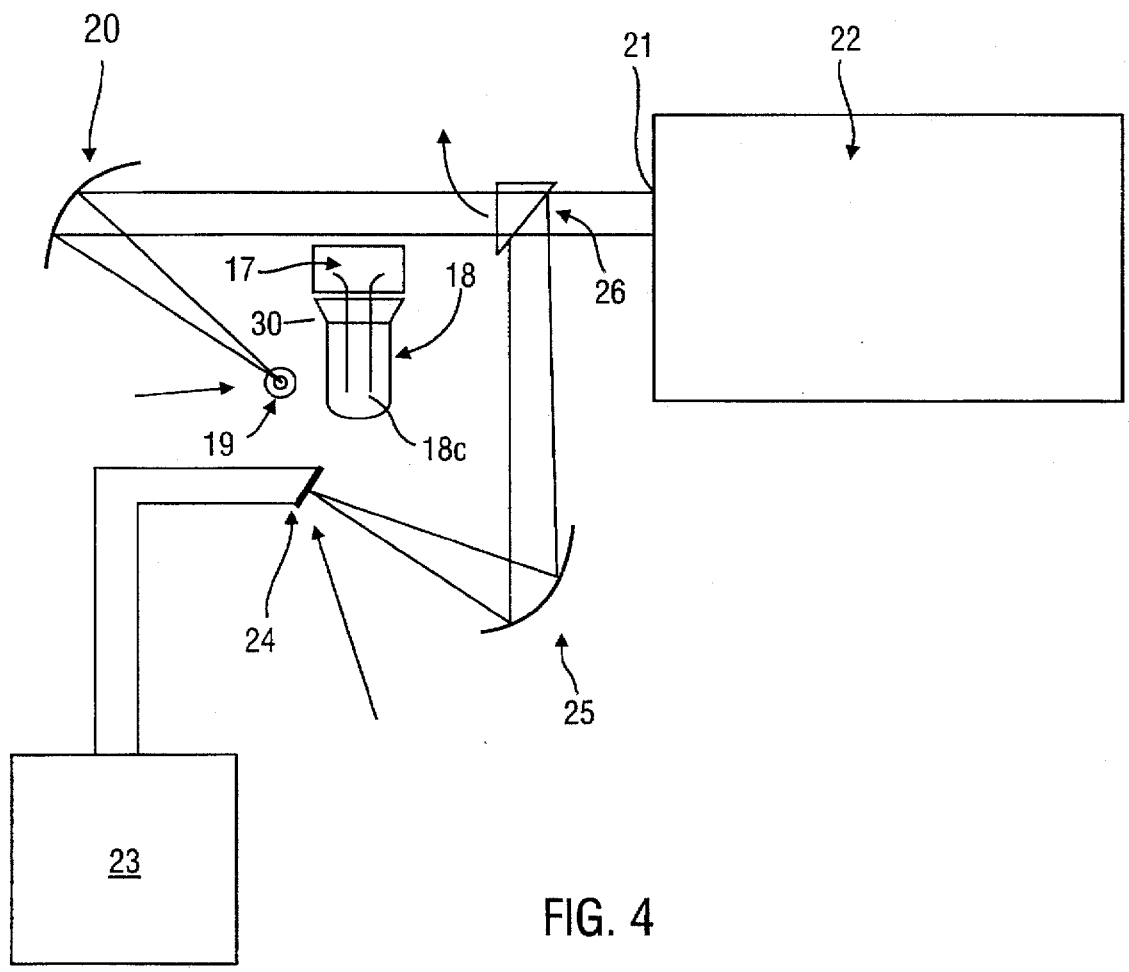
FIG. 4 is a simplified schematic diagram of an ID-FIRE detection system used in some of the following experiments.

ID-FIRE Instrumental Configuration. FIG. 4 shows a schematic diagram of an ID-FIRE analytic system embodiment used in Examples 1 and 2. The apparatus shown in FIG. 4 consists of five major sections: the blackbody source 24, the electrolysis cell 18, the burner 19, the FTIR 22 and the exhaust system 30.

Figure 5:
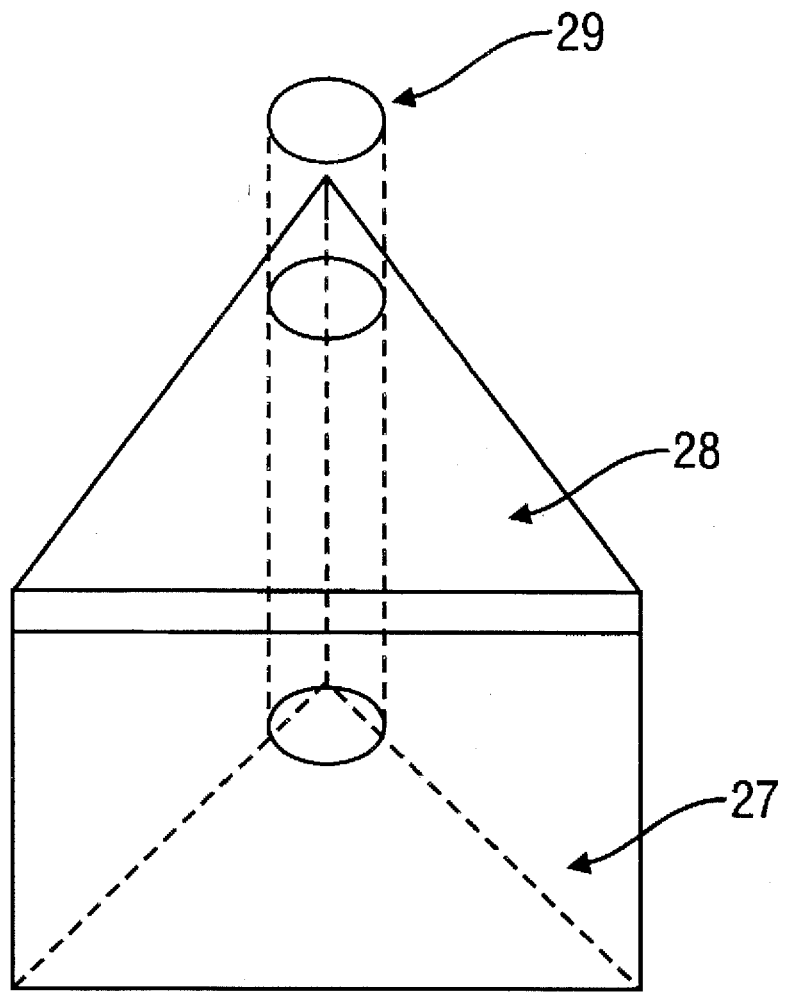
FIG. 5 is a simplified diagram of one embodiment of a moveable mirror assembly used to selectively direct radiation from a blackbody source into the emission port of a Fourier-transform infrared spectrometer (FTIR).

The FTIR was modified for use in emission studies rather than absorption by disconnecting the original source and opening the external emission port on the side of the instrument. An intense blackbody source 24 was substituted for the original. The blackbody source was needed only to initialize the instrument used in this example. With proper modification of software it would be unnecessary. The blackbody source 24 included a coil of Nichrome heating wire wound around a ceramic tube (¼" OD and 2" long) and connected to a 110 V variable transformer 23. This served as the source needed to initiate the FTIR. The radiation from the hot wire coil was collimated by a 30 cm from surfaced spherical mirror 25 placed 30 cm from the coil. The mirror was purchased from Eating Electro-Optics, Holliston, Mass. (#34-9845). The collimated beam was directed into the emission port of the FTIR by the 2"×2" flat front surfaced mirror (Eating #23-4203) of a moveable mirror assembly 26. By "moveable", it is meant that a mirror assembly is constructed to be capable of being selectively positioned to direct radiation from a blackbody source to an FTIR, and is further capable of being moved to another position that is out of the light path of the FTIR once the FTIR is initiated. In the embodiment of this particular example, the moveable mirror assembly 26 was placed 57 cm from the spherical mirror 25, and was constructed by mounting a flat mirror 27 on the side of a triangular block of aluminum 28 with a rod 29 through one corner as shown in FIG. 5. So constructed, the mirror was capable of swinging out of the light-path between the burner 19 and the FTIR 22 when spectra from the flame were being collected. After initiating the FTIR 22 the blackbody source 24 was turned off and the moveable mirror assembly 26 was swung out the path of the burner.

Radiation from the burner 19 was collected by the 30 cm from surfaced mirror 20 placed 30 cm from the burner 19, 53 cm from the FTIR 22, and set at an angle capable of directing the collimated light into the emission port of the FTIR 21. The mirrors 20 and 25 are identical, having the same part number.

Electrolysis Cell

In the following ID-FIRE examples, chlorine gas from aqueous chloride solutions was produced electrolytically using the electrolysis cell 31 depicted in FIG. 6. This electrolysis cell was constructed in the laboratory from 2 cm diameter Pyrex tubing cut to a length of 6.5 cm. A side arm 32 for the cell was constructed from 6 mm OD Pyrex tubing that was cut to a length of 2 cm and attached to the side of the cell 32 as shown. The side arm 32 was positioned 4 cm from the bottom of the cell. A Teflon stopper 33 was machined in the laboratory and inserted into the top of the glass cell 31. The Teflon stopper 33 was fitted with an O-ring 34 to prevent leaking of gaseous products between the stopper 33 and the glass cell 31. Holes for electrodes 35 and 36, and gas dispersion tube 37, were drilled to an exact diameter into the Teflon stopper 33 so that a "gas-tight" fit with each of these components was achieved. This eliminated the need for any adhesive while still preventing gas leaks. The gas dispersion tube 37 was purchased from Ace Glass Inc., Louisville, Ky. (Cat. #9435-D, porosity 10–20 m). The chlorine produced at the anode 35 was purged out of the cell through and into the burner flame 38 using hydrogen gas 39 maintained at a flow rate of 8 mL/min through the gas dispersion tube 37. The electrodes 35 and 36 were constructed of Pt/20% Ir, and were each 0.0625" OD and 10 cm long. The Pt/20% Ir for the electrodes 35 and 36 was purchased from Nobel-Met, Limited, Roanoke, Va. A power supply 40 from Electro Industries, Chicago, Ill. (Model #3002A) set at a current of 2 amps and an applied potential of 5 volts was the source of power to the electrodes 35 and 36. All gas connections were made using ⅛" OD×1/16" ID Teflon tubing 41 with Teflon Swagelok fittings and ferrules 42.

Capillary Burner

Figure 7:
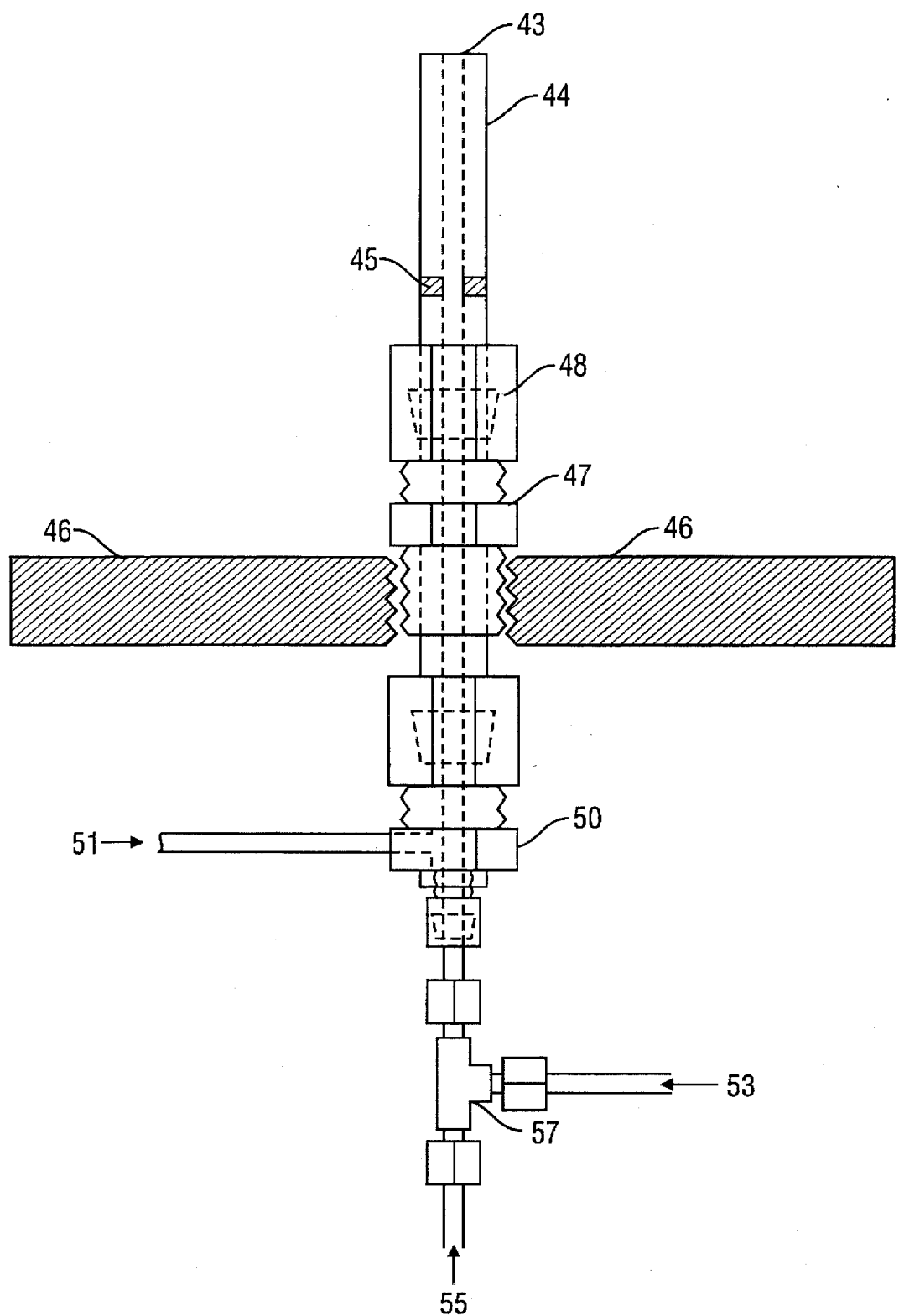
FIG. 7 is a simplified schematic diagram of a ceramic concentric two-tube burner used in some of the following experiments.

FIG. 7 shows a schematic diagram of a burner embodiment employed in the following ID-FIRE examples. The burner consists of two ceramic tubes of different diameters, 43 and 44, mounted concentrically. Due to the corrosive action of chlorine and hydrogen chloride gases at flame temperatures, it was necessary to construct the burner from materials inert to the burning of chlorine gas in the burner flame. It was found that ceramic material or quartz works quite well. In this case, ceramic tubing was used. The ceramic tubing used for the burner was Omegamite 450 (99% $Al_2O_3$) purchased from Omega Corp., Stamford, Conn. The outer tube 44 was ¼" OD×5/32" ID (Cat. #ORX1814). The inner tube 43 was ⅛"×1/16" ID (Cat. #ORA11618-6). Glass wool 45 was packed between the tubes to diffuse the flow of air, oxygen or other gases input via inlet 51 when used. Chlorine gas from the electrolysis cell was supplied to the inner tube through sample inlet 53 connected to the inner tube by a ⅛" Teflon tee 57. Hydrogen gas was input to the inner tube through inlet 55.

The outer tube 44 was mounted to a 4½"×5½" aluminum plate 46 using a ¼" brass NPT to Swagelok connector 47 and held in place by a graphite reducing ferrule 48. The inner tube 43 was positioned inside the outer tube 44 by the glass wool plug 45 and held in place by a ¼" to ⅛" brass Swagelok reducing fitting with graphite ferrule 50. Recession of the inner capillary tube 43 about 2 mm below the outer tube 44 at the burner tip was found to be beneficial in reducing background radiation and improving flame stability. Inlet 51 was constructed of ⅛" copper tubing soldered to a hole drilled into the ¼" to ⅛" brass Swagelok fitting so as to communicate with the outer tube 44 as shown.

Although certain types and sizes of laboratory equipment were employed in the burner embodiment of this example, it will be appreciated by those skilled in the art that particular apparatus parameters, such as fitting types and tubing diameters, are well known to the art and not critical to the practice of the present invention. It will be further appreciated that benefits of the present invention may be obtained using burner embodiments of the apparatus of the present invention constructed in a variety of ways known to those skilled in the art using different fitting types, tubing diameters, etc.. Furthermore, in the absence of any particular details, those skilled in the art will understand how a burner for hydrogen/chlorine combustion in the present invention may be constructed using equipment known to the art.

Exhaust System

Figure 8:
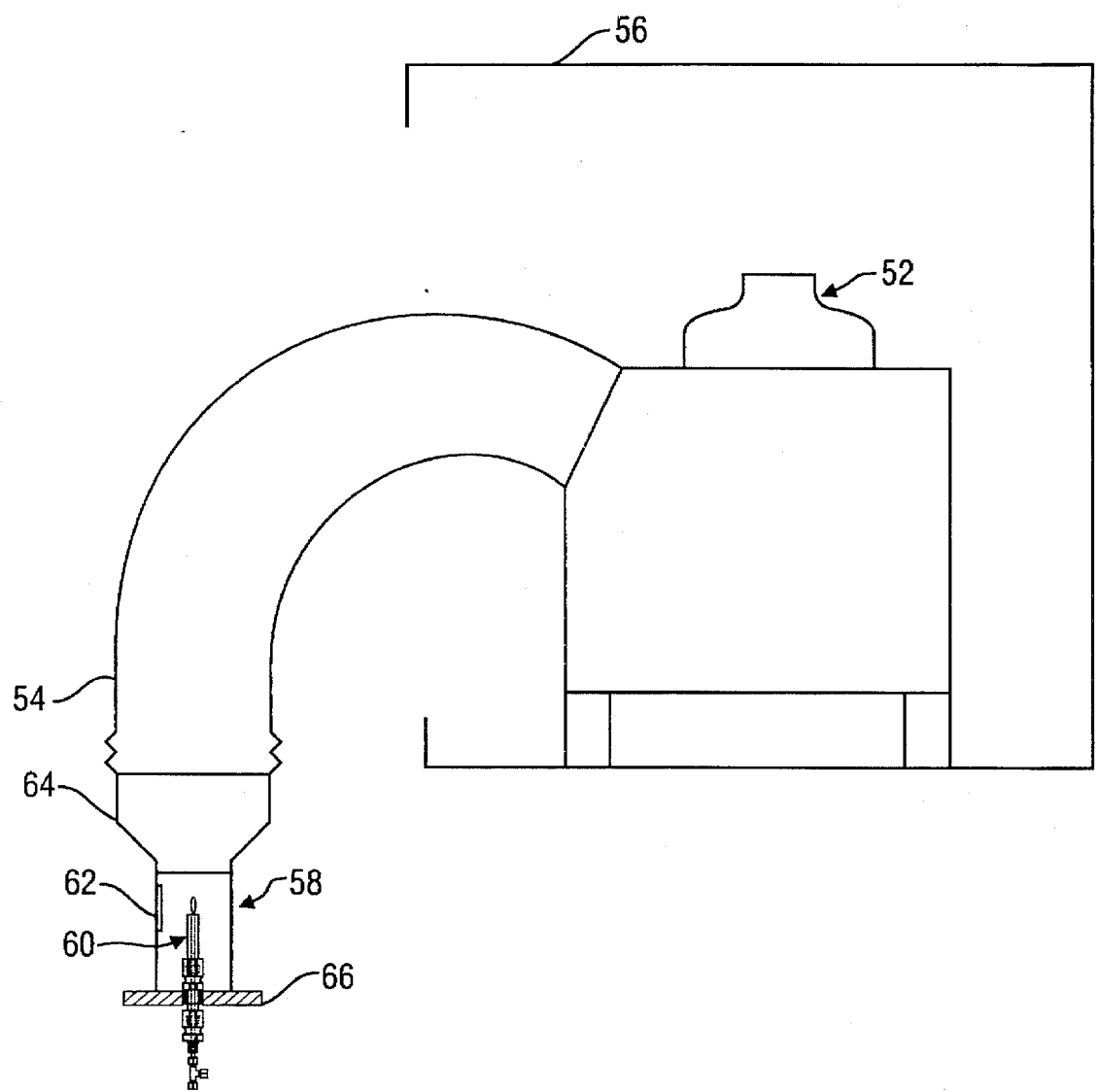
FIG. 8 is a simplified schematic diagram of an exhaust system used in some of the following experiments.
Figure 9:
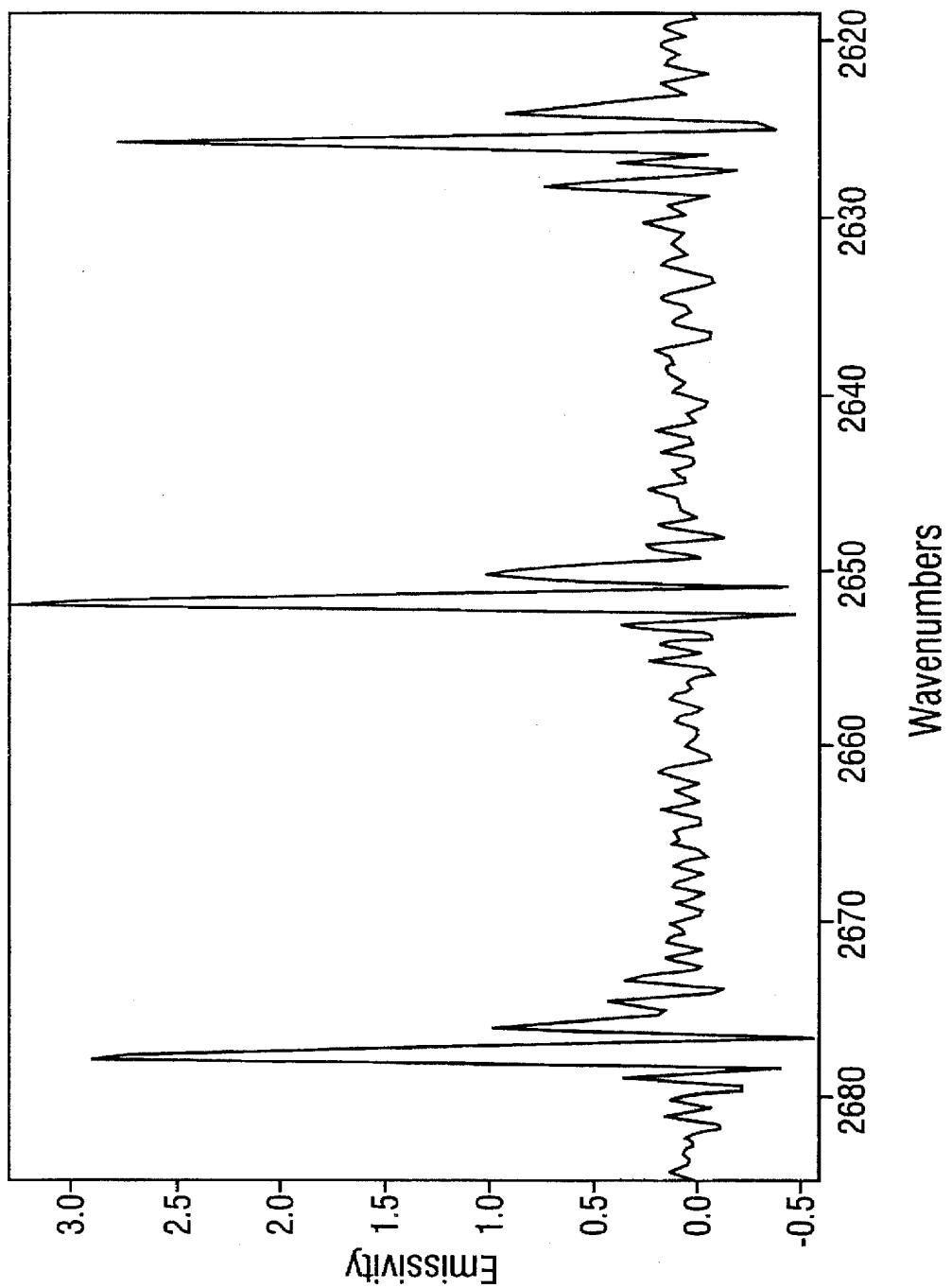
FIG. 9 is a flame infrared HCl emission spectrum of the non-isotopically enriched prepared first sample of Example 1.
Figure 10:
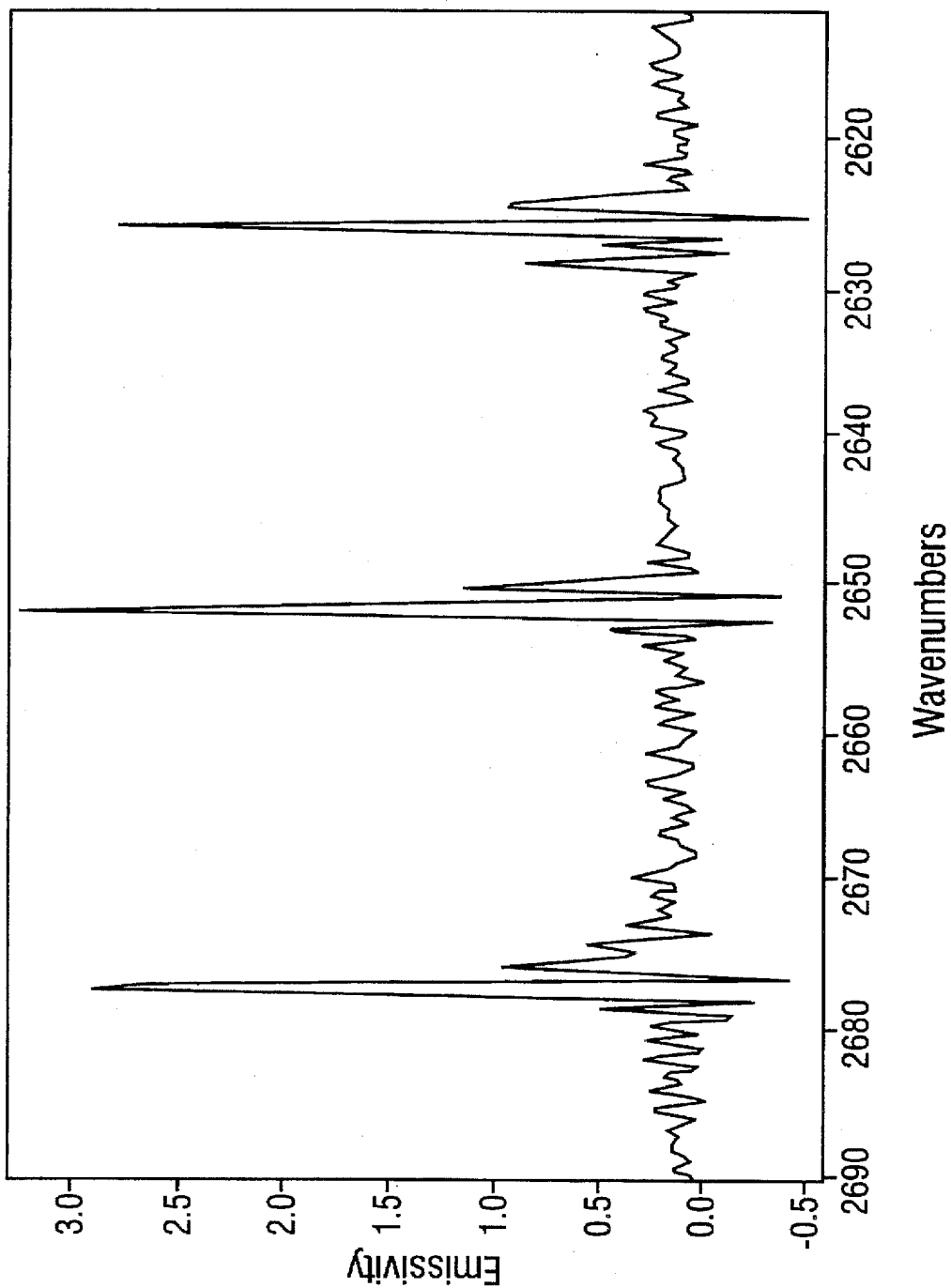
FIG. 10 is a flame infrared HCl emission spectrum of the non-isotopically enriched prepared first sample of Example 1.
Figure 11:
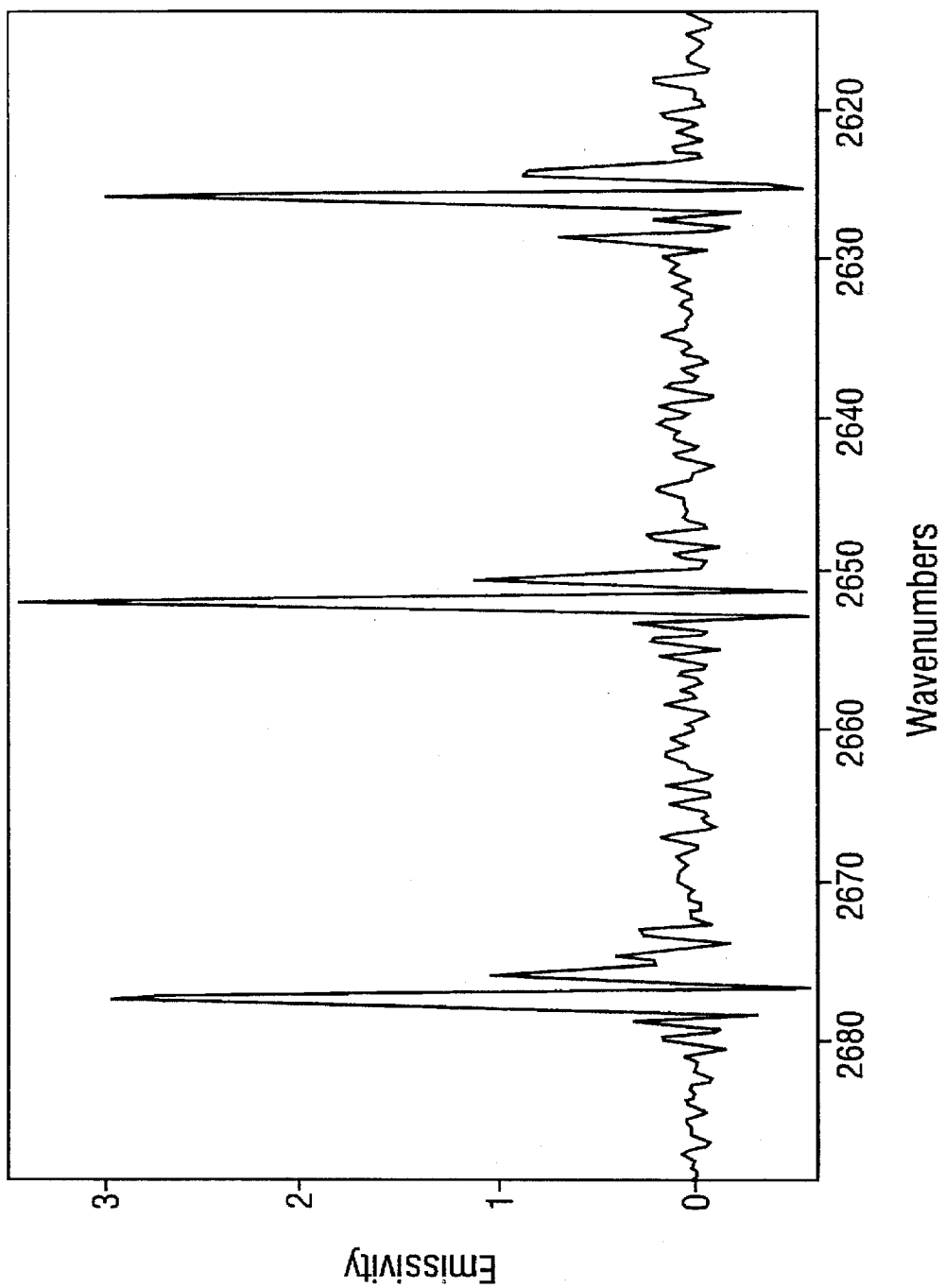
FIG. 11 is a flame infrared HCl emission spectrum of the non-isotopically enriched prepared first sample of Example 1.
Figure 12:
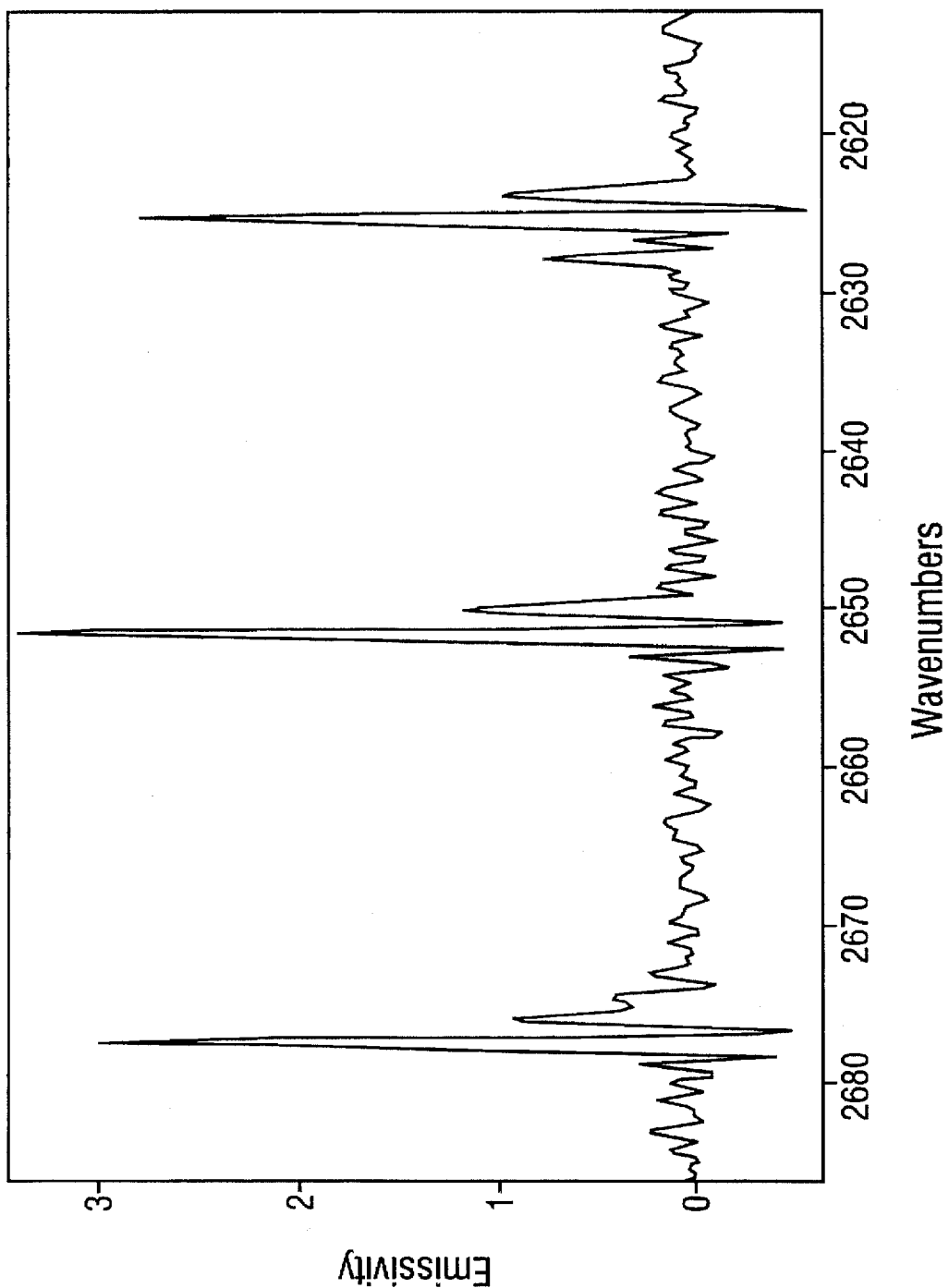
FIG. 12 is a flame infrared HCl emission spectrum of the non-isotopically enriched prepared first sample of Example 1.

The electrolysis and combustion products, namely chlorine and hydrogen chloride, pose a potential health hazard as well as being quite corrosive to instruments located nearby if any gases are released into the laboratory environment. The exhaust system embodiment shown in FIG. 8 was designed to safely remove these gases from the laboratory.

An Ametek vacuum motor (Model #116392-00), Lamb Electric Div. 52, powered by a variable auto transformer provided the suction to draw gases through a duct 54 to the fume hood 56 for removal from the building. A burner chamber 58 was constructed of 2" ID PVC tube to house the burner 60. The 2" PVC tube 58 was fitted with a $CaF_2$ window purchased from Salon Technology, Inc., Salon, Ohio, Cat. #04103 (41 mm diameter×3 mm thick) 62. The window was placed in the side of the burner chamber 58 to allow the infrared radiation to reach and be detected by the FTIR.

A 2"×4" PVC reducing fitting 64 was used to attach plastic flexible 4" dryer duct 54 to the 2" PVC tube 58. The 2" PVC tube was sealed to aluminum plate 66 with silicon seal cement (using G.E. Silicone II Household Glue and Seal).

Reagents

All chemicals were ACS reagent grade and were used without further purification. 3M of $H_2SO_4$ was prepared by diluting concentrated $H_2SO_4$ with deionized water. Standard and isotopically enriched NaCl solutions were prepared by dissolving NaCl (dried at 120° C. for 24 hours) in 3M $H_2SO_4$. Isotopically enriched NaCl was purchased from Cambridge Isotopes and certified to be 95.0% $Cl^{37}$ and 5.0% $Cl^{35}$.

FTIR

The FTIR embodiment used in these examples was a Mattson Galaxy Series 5000 (Model GL-5020), Mattson Instruments Inc., Madison, Wis., equipped with a deuterated triglycine sulfate (DTGS) detector. The instrument was modified for flame infrared emission measurements by disconnecting the original internal source and substituting a "red hot wire coil" located outside the unit as a source to activate the instrument. The FTIR was equipped with a 486/33 Hz computer with Windows using the "WIN FIRST" software program, commercially available from Mattson Inc., for collecting and processing the spectral data.

Although not specifically incorporated in this embodiment, a multiple mirror collection optical system such as that described by Busch et at., Applied Spectroscopy 45:964–968 (1991) may be employed for the purpose of increasing the solid angle of radiation collected by an FTIR. In this embodiment, mirrors $M_1$, $M_2$, and $M_3$ in FIG. 1 of the aforementioned reference would be located around the flame. This would require adding more windows to the burner chamber 58 in FIG. 8. Spherical mirror $M_3$ in FIG. 4 would replace the lenses $L_1$ and $L_2$ in FIG. 1 of the reference.

While not specifically incorporated in the experimental apparatus, it should be understood that cooled detectors can be used with the FTIR in place of the room temperature detectors that were employed in these examples. Thermo-electrically cooled detectors are commercially available. Cooling extends the long wavelength response and increases the specific detectivity (D✰) of the detector. Furthermore, it should be understood that other emission sources can be used with the FTIR described above. Such sources include electrically heated furnaces and various types of electrical discharges.

Experimental Procedure and Results

For this example, the experimental apparatus described above was used to quantitatively determine the chloride ion concentration in a prepared first sample by mixing the first sample with a second sample containing isotopically enriched chlorine. In this example, $^{37}Cl$ was used as the chosen isotope to isotopically enrich the chlorine of the second sample. The first sample was prepared by dissolving 11.8500 g of dried NaCl in 100 mL of deionized water. This first sample of known concentration contained a "natural abundance" of $^{37}Cl$ to $^{35}Cl$. The second sample was prepared by dissolving 500 mg of isotopically enriched NaCl (containing 95% $^{37}Cl$ and 5% $^{35}Cl$) in 25.00 mL of deionized water.

The natural abundance of chlorine is reported to be about 75.77% $^{35}Cl$ and about 24.23% $^{37}Cl$. *Encyclopedia of Science and Technology*, Volume 9, pp 454–456. However, the natural abundance of isotopic ratios can change slightly from sample to sample. It is, therefore, important to determine the ratio of $^{37}Cl$ to $^{35}Cl$ in each sample before spiking the sample with the enriched isotope.

In this example, the natural abundance of $^{37}Cl$ to $^{35}Cl$ was first determined for the first sample as follows using one embodiment of the ID-FIRE technique of the present invention and the following procedure. The experimental apparatus used in this example is schematically illustrated in FIG. 4.

Prior to collecting spectral data, the electrolytic cell 18 was filled with 2 mL of the aqueous NaCl solution of the first sample using a 2 mL glass pipet (Class A). Both the $H_2$ flow 19a to the burner 19 and the electrolysis cell purge 19b were turned on, the exhaust system 30 activated, and the burner 19 ignited. This was done in order to allow the hydrogen flow and the flame to stabilize. While the flame was stabilizing, the FTIR 21 was initiated. The wire coil 24 was heated until red-hot, the moveable mirror assembly 26 was rotated in position to direct the blackbody radiation into the emission port 21 of the FTIR 22. The FTIR and computer were then turned on. When the FTIR was ready to collect data, the heating coil was turned off and the moveable mirror 26 was rotated out of the optical path of the burner. The power supply 17 to the electrolysis cell platinum electrodes 18c was turned on and the rotational spectrum of HCl was collected between 3200 and 2400 $cm^{-1}$. From this spectrum, it was possible to calculate the natural abundance ratio of $^{37}Cl$ to $^{35}Cl$ in each aliquot of the non-enriched first sample analyzed.

Four 2 mL aliquots of the non-isotopically enriched first sample were analyzed as above to obtain an average natural abundance ratio of $^{37}Cl$ to $^{35}Cl$ (Rs) in the first sample. The emission spectra obtained from these four runs are presented in FIG. 9–FIG. 12 (spectra #08019503–08019506). From this calculated average ratio (Rs), the fractional amounts of $^{37}Cl$ (As) and $^{35}Cl$ (Bs) present in the first sample were then calculated as follows.

First, given that:

$$As+Bs=1 \text{ (or 100\%)},$$

and given that:

$$As/Bs=Rs,$$

then substituting:

$$As=Rs/(1+Rs)$$

The peak heights of the strongest emission line-pair located at 2650.7 $cm^{-1}$ and 2651.77 $cm^{-1}$ in each of the spectra of FIG. 9–FIG. 12 were used for the calculation. The line pairs of the four trials had peak heights with approximate emissivity values of 0.97 and 3.28, 1.09 and 3.25, 1.09 and 3.41, and 1.13 and 3.39, respectively. This yielded Rs values of 0.2957, 0.3354, 0.3196, and 0.3333. The average ratio (Rs) of peak heights of the four trials was calculated to be 0.3213. Using the above equations, the natural abundance values of As and Bs were calculated to be 0.243 and 0.757, respectively. This translates into a natural abundance of chlorine isotopes present in the first sample equal to 24.3% $^{37}Cl$ and 75.7% $^{35}Cl$. It should be noted that the method of the present invention may also be used to determine the fractional abundance of chlorine isotopes in a chlorine-containing sample having other than the natural ratio of abundance of chlorine isotopes.

Figure 6:
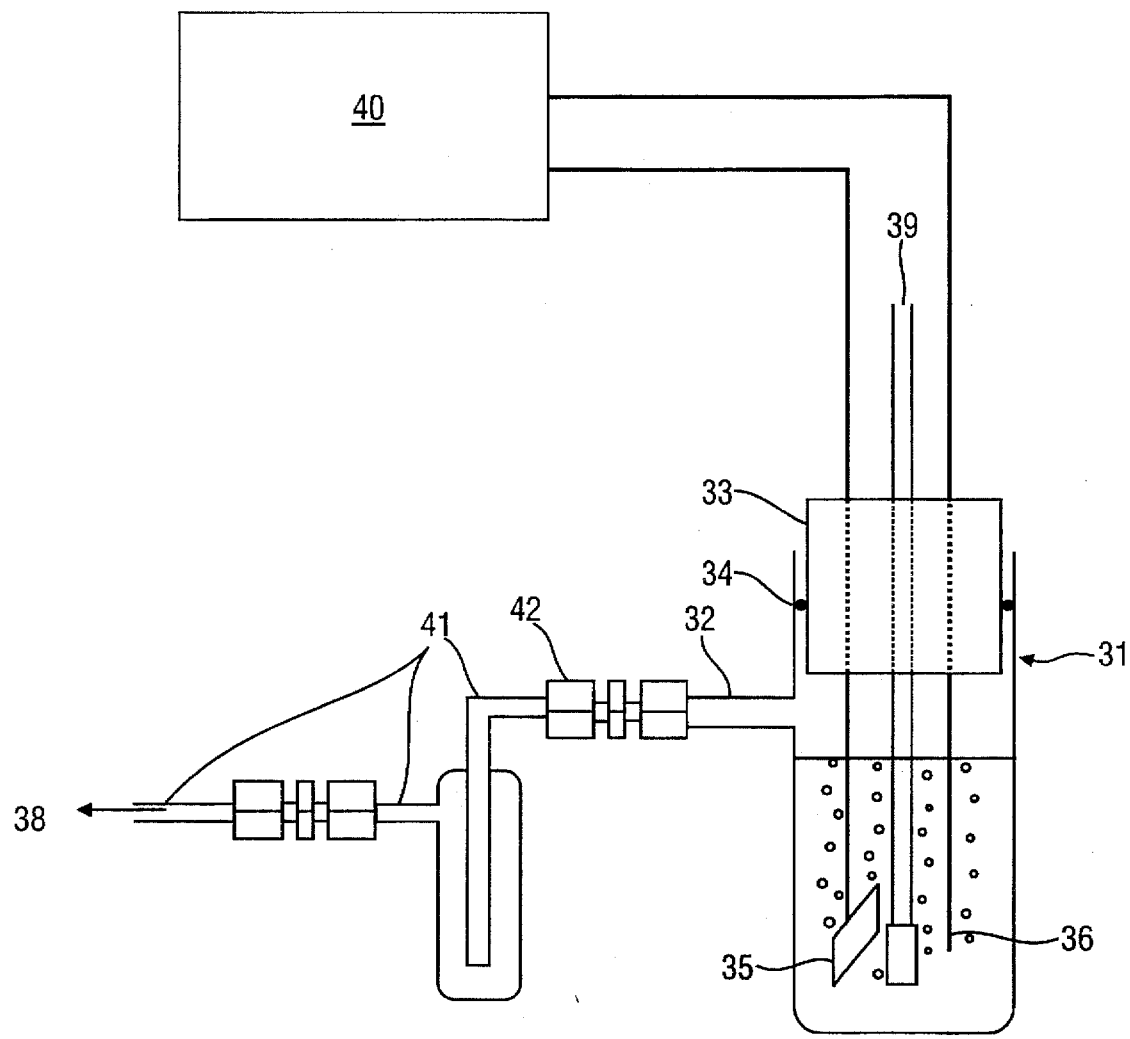
FIG. 6 is a simplified schematic diagram of an electrolytic cell used in the following experiments.

Next, referring to FIGS. 6 and 7, the isotopically enriched $Na^{37}Cl$ second sample was mixed with the first sample for the ID-FIRE determination of chloride ion concentration in the first sample. Prior to this determination, the power to the electrodes 35 and 36 was turned off, the Teflon stopper 33 was removed from the electrolytic cell 31, and the waste solution from previous analyses removed. The cell was rinsed with deionized water and dried with a tissue.

A 2.00 mL aliquot of the non-isotopically enriched first sample (containing the determined natural abundance ratio of 0.243 $^{37}Cl$ and 0.757 $^{35}Cl$) was then pipetted into the electrolysis cell 31. A 1.0 mL aliquot of the isotopically enriched NaCl second sample (containing 95% $^{37}Cl$ and 5% $^{35}Cl$) was added to the sample using a 500 mL Oxford P-7000 Sampler System pipet. The Teflon stopper 33 was placed on the electrolysis cell 31 and the hydrogen purge 39 was started and allowed to run for several minutes to be sure that the two samples were completely mixed. The flow of air 51 and $H_2$ 55 to the burner was started and the burner flame ignited.

The FTIR was turned on and initialized for data collection. The power supply 40 to the electrodes 35 and 36 was then turned on, causing chloride ions in the electrolysis cell solution to be converted to $Cl_2$ chlorine gas. This $Cl_2$ gas was then swept into the flame where it was converted to excited HCl molecules. The FTIR spectrometer was then activated and 50 spectral scans of the HCl rotational spectrum were collected between 3200 $cm^{-1}$ and 2400 $cm^{-1}$ by the interferometer. The data was then processed by the computation means to produce an infrared emission spectrum.

Figure 13:
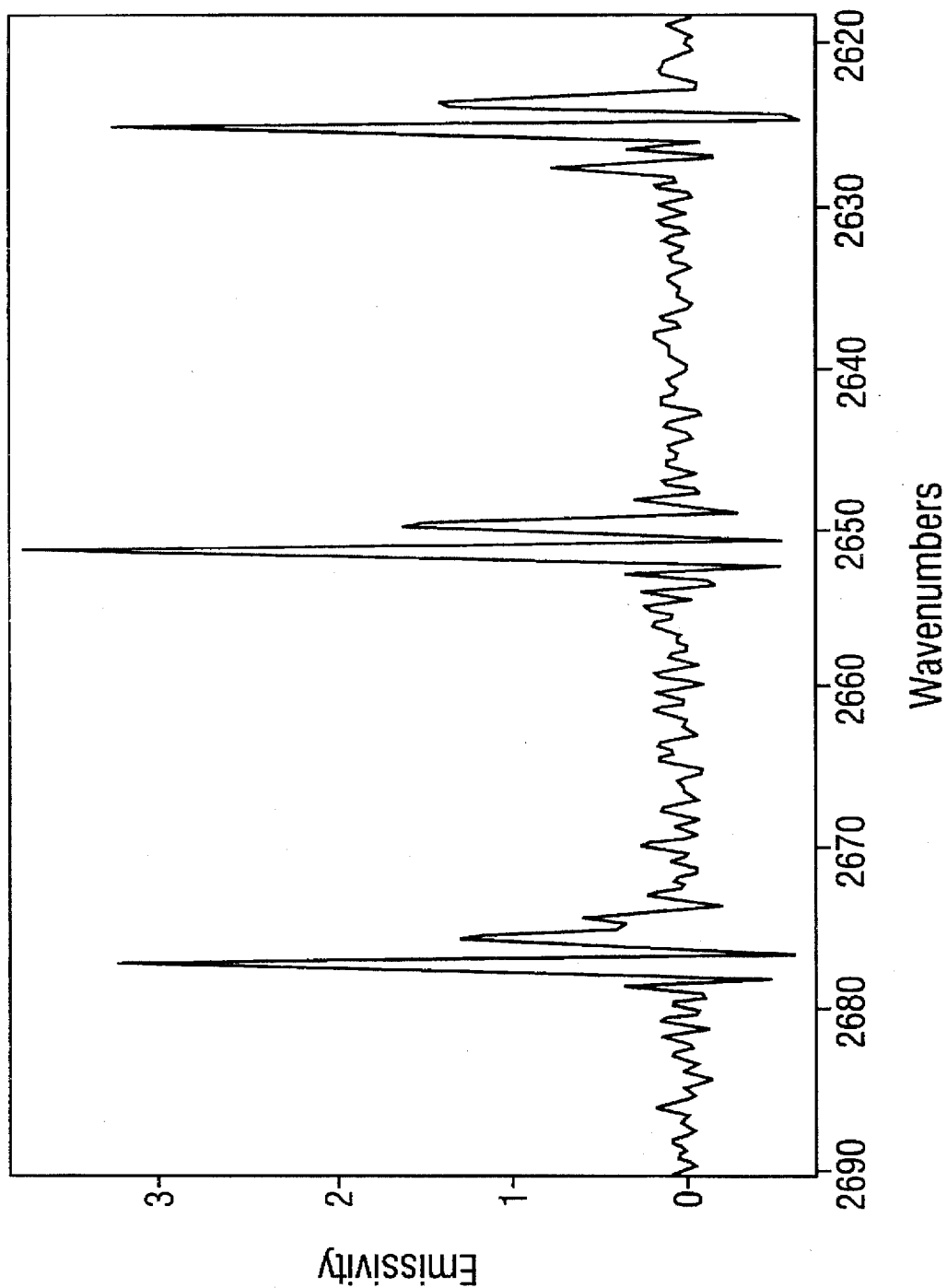
FIG. 13 is a flame infrared HCl emission spectrum of a mixture of the non-isotopically enriched first sample and isotopically enriched second sample of Example 1.

FIG. 13 (spectrum #08019507) is the flame infrared emission spectra generated by the combustion of the vibrationally excited HCl of this example, with the strongest separate $H^{37}Cl$ and $H^{35}Cl$ emission line-peaks again clearly visible at wavelengths of 2650.7 $cm^{-1}$ and 2651.77 $cm^{-1}$, respectively. In this spectrum, the HCl emission line-peak at 2650.7 $cm^{-1}$ has an emissivity value of about 1.59, and the HCl emission line-peak at 2651.77 $cm^{-1}$ has an emissivity value of about 3.74. Based on the ratio of these emissivity values, the ratio of $^{37}Cl$ to $^{35}Cl$ (RM) was calculated from the peak heights to be 0.4251. In this example, the isotopically enriched second sample contained 0.4861 grams of enriched NaCl dissolved in 25.00 ml of solution. This translates to a concentration of 0.01945 g NaCl/mL and 0.0118 g $Cl^-$/mL.

ID-FIRE Calculation of Chloride Ion Content

Calculations of the concentration of chloride in the sample were then made using the following equation of the form given by Fassett and Paulsen, (1989).

$$Cs = \frac{(Csp)(Vsp)}{Vs} \times \frac{Asp - [(Rm)(Bsp)]}{[(Rm)(Bs)] - As}$$

where:
Cs=concentration of chloride ion in the first sample (unknown)
Csp=known concentration of chloride ion in the isotopically enriched second sample=0.0118 g $Cl^-$/ml
Vsp=volume of the isotopically enriched second sample mixed with the first sample=0.9748 ml
Vs=volume of the first sample used=1.9569 ml
Rs=natural abundance ratio of the chosen chlorine isotope (here $^{37}Cl$) to the other chlorine isotope (here $^{35}Cl$) in the first sample=0.3213
As=natural abundance fraction of the chosen chlorine isotope (here $^{37}Cl$) in the first sample=0.2432
Bs=natural abundance fraction of the other chlorine isotope (here $^{35}Cl$) in the first sample=0.7568
Asp=fraction of the chosen chlorine isotope (here $^{37}Cl$) in the isotopically enriched second sample=0.95
Bsp=fraction of the other chlorine isotope (here $^{35}Cl$) in the isotopically enriched second sample=0.05
Rm=measured ratio of the chosen chlorine isotope (here $^{37}Cl$) to the other chlorine isotope (here $^{35}Cl$) determined from the HCl infrared spectrum of the mixture of the first and second solutions=0.4251

Substituting the above values into the equation given above:

$$Cs = \frac{(0.0118 \text{ g } Cl^-/mL)(0.9748 \text{ mL})}{1.9569 \text{ mL}} \times \frac{(0.95) - [(0.4251)(0.05)]}{[(0.4251)(0.7568)] - (0.2432)}$$

$$Cs = 0.0695 \text{ g } Cl^-/ml$$

The actual weighed amount of chloride ion present in the first sample was 0.0719 g/ml. Therefore, the fractional error of the ID-FIRE chloride determination made in this example may be calculated using the following equation:

Error=[(ID-FIRE Cs)−(Actual Cs)]/(Actual Cs), or

Error=(0.0719−0.0695)/(0.0719)=(0.0024)/(0.0719)=0.0334 (or 3.34%)

Example 2—Quantitative Chloride Ion Determination in an Unknown Aqueous Sample Using $^{37}Cl$ as the Chosen Isotope

Experimental Procedure and Apparatus

Using the procedure and apparatus of Example 1, a first sample of water from the Gulf of Mexico having an unknown chloride ion concentration was analyzed to determine the chloride ion content. The ratios of $^{37}Cl$ to $^{35}Cl$ for the unknown first sample and the isotopically enriched second sample were obtained from the IR spectra as described in Example 2.

Figure 14:
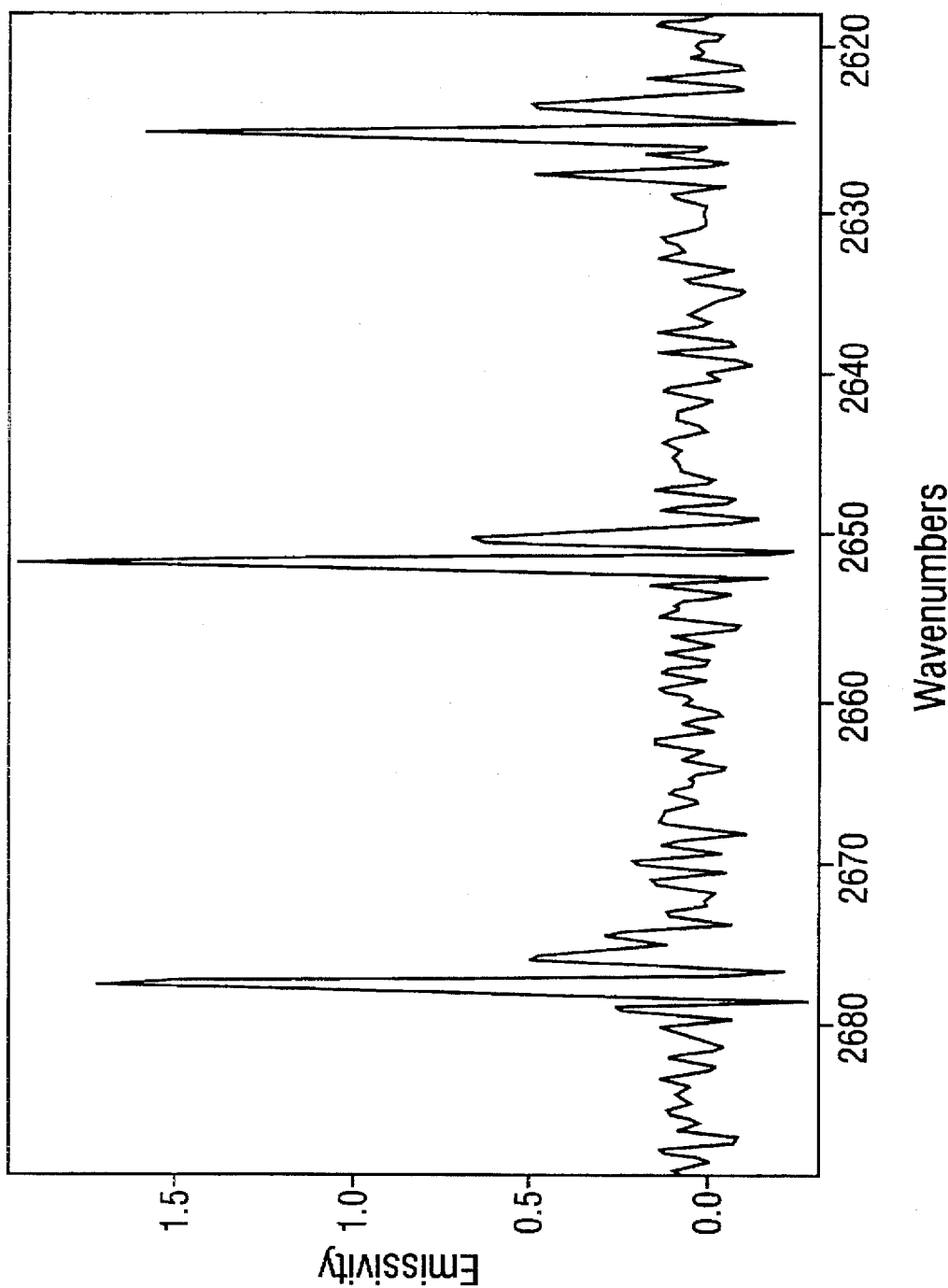
FIG. 14 is a flame infrared HCl emission spectrum of the non-isotopically enriched unknown first sample of Example 2.

The infrared spectra for the non-isotopically enriched first sample is shown in FIG. 14 (Spectrum #08099505). From this spectra, the natural abundance ratio of $^{37}Cl$ to $^{35}Cl$ (Rs) in the first sample was calculated to be 0.3333. The natural abundance values of As and Bs were calculated to be 0.24998 and 0.75002, respectively.

Figure 15:
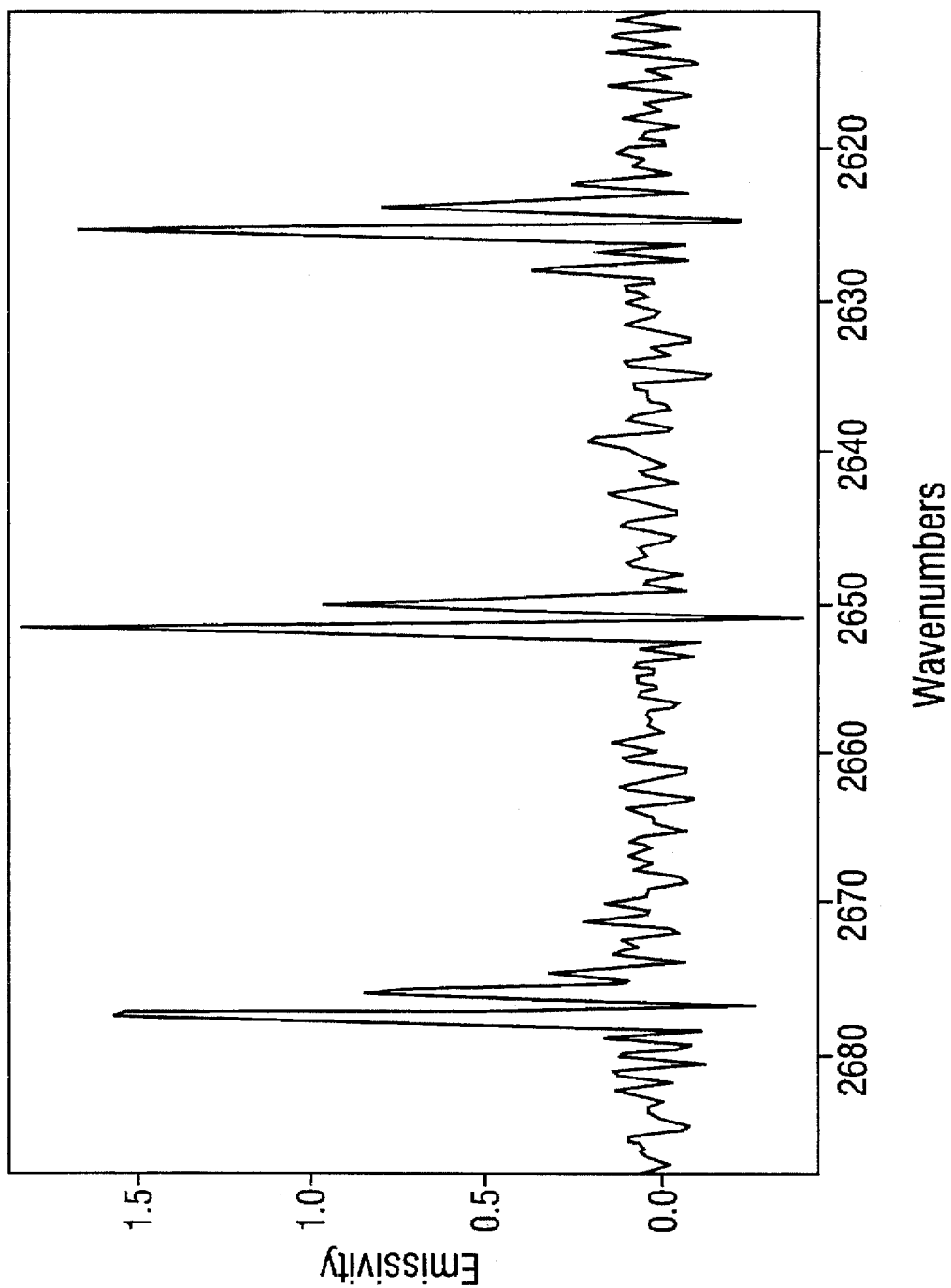
FIG. 15 is a flame infrared HCl emission spectrum of a mixture of the non-isotopically enriched first sample and isotopically enriched second sample of Example 2.

The infrared spectra for the mixture of isotopically enriched second sample with the non-isotopically enriched first sample is shown in FIG. 15 (spectrum #08099507). In this spectra, the HCl emission line-peak at 2650.7 $cm^{-1}$ has an emissivity value of about 0.95, and the HCl emission line-peak at 2651.77 cm$^{-1}$ has an emissivity value of about 1.82. Based on the ratio of these emissivity values, the ratio of $^{37}$Cl to $^{35}$Cl (Rm) was calculated to be 0.5220.

ID-FIRE Results and Calculation of Chloride Ion Content

Using the procedure of Example 1, the following results were obtained:
Vs=1.9844 ml
Rs=0.3333
As=0.24998
Bs=0.75002
Csp=0.0118 g Cl$^-$/ml
Vsp=0.5046 ml
Rm=0.5220
Asp=0.95
Bsp=0.05

Using the equation described in Example 1:

$$Cs = \frac{(Csp)(Vsp) \times Asp - [(Rm)(Bsp)]}{Vs\,[(Rm)(Bs)] - As} \quad 1)$$

$$Cs = \frac{(0.0118\ g/mL)(0.5046\ mL)}{1.9844\ mL} \times \frac{(0.95) - [(0.5220)(0.05)]}{[(0.5220)(0.7502)] - (0.24998)}$$

$Cs = 0.01959$ g Cl$^-$/mL
or $Cs = 19,590$ mg Cl$^-$/L

For comparison purposes, the first sample of Gulf Water was also analyzed for chloride ion content by Microbac Laboratories Inc. in Brownsville, Tex. with argentometric titration methods using silver nitrate and potassium chromate indicator. This titration yielded a chloride ion concentration of 19,488 mg Cl$^-$/L. Therefore the percent difference between the chloride content values yielded by the ID-FIRE and titration methods can be calculated as follows:

% Difference =

$$\frac{(ID-Fire\ Cs) - (Titration\ Cs)}{Titration\ Cs} = \frac{19,590 - 19,488}{19,488} \quad 100$$

% Difference = 0.523%

The minimal difference in the chloride ion concentration determined by the two methods illustrates that the ID-FIRE technique may be used to obtain chloride ion content values of similar accuracy to existing methods, but without the problems associated with such methods.

Example 3—Chlorine Detection in Chlorine Containing Liquid Compounds

The following example illustrates the detection of chlorine in various chlorine containing compounds using flame infrared emission spectrometry (FIRE). Although the FTIR apparatus employed in this example was not set for maximum resolution (in this experiment, the instrument was set for a resolution of about 4 cm$^{-1}$, however a resolution of about 0.75 cm$^{-1}$ or better is needed), it had sufficient resolution to demonstrate that in principle, high resolution spectra can be obtained from the exposure of chlorine-containing liquids to combustion flames.

In this example, a miniature capillary-head burner (Hudson and Busch, 1988) was modified for use with liquid samples. As the previously designed burner was intended to admit a gas stream from the gas chromatograph to the center of the burner-head, the burner was modified for nebulized liquid samples. The central sample injection capillary was removed, and the number of small-bore capillary tubes in the burner-head was increased from 6 to 19 (the internal diameter of the capillary tubes was 0.6 mm). The overall diameter of the burner orifice was 0.5 cm. The capillary-head burner was fitted with a Janell-Ash model X-88 atomic absorption cross-flow nebulizer and a 3 cm long×4 cm diameter TEFLON spray chamber. The nebulizer and spray chamber were coupled to the burner body by boring a one inch hole in the side of the burner body (perpendicular to the capillary-head) and press fitting the spray chamber/nebulizer assembly to the burner.

A 1:1 hydrogen/air flame stoichiometry was used for all measurements, and the fuel and oxidant flow-rate were maintained at 200 mL/min. A 1:1 fuel/oxidant mixture resulted in a stable flame about 4 cm in height by 1 cm in width. The infrared emissions were observed over a 0.6 cm vertical segment centered at a height of 1.5 cm from the burner top. The reagent grade liquid samples were introduced into the flame via aspiration by the nebulizer.

All flame infrared emission spectra were acquired on an unpurged Mattson Cygnus 100 Fourier transform spectrometer. Fourier transform infrared emission spectroscopy allows multi-wavelength analysis. The Fourier transform spectrometer, by virtue of the multiplex nature of the data acquisition, is a multichannel instrument and can therefore monitor all infrared wavelengths simultaneously. Since the desired molecular emission occurs in the infrared spectral region, any standard, commercially available Fourier transform-spectrometer can be utilized without the need for special optics, beamsplitters, or detectors. The Fourier transform instrument also provides several advantages for infrared emission spectroscopy. These advantages include: a single instrument for both elemental and molecular analysis, high optical throughput, good spectral resolution, accurate wavelength recording due to the reference laser, the ability to signal average by coaddition, and the capability of performing spectral subtraction.

Figure 16:
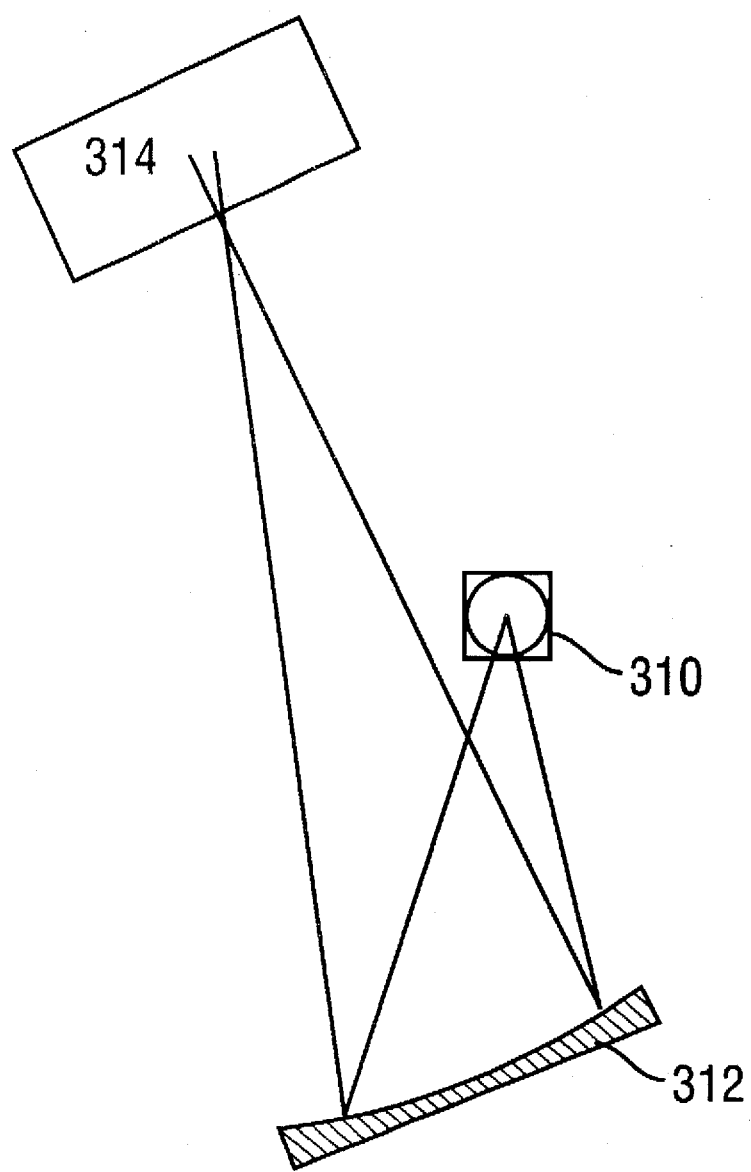
FIG. 16 schematically illustrates the experimental set up of a burner, mirror and Fourier transform spectrometer for Example 3.

FIG. 16 schematically shows the arrangement of the burner 310, mirror 312 and Fourier transform-spectrometer 314 for Example 3. A 5-cm-focal-length, 10-cm-diameter aluminum mirror 312 was used to collect and collimate the infrared emissions from the flame. It should be noted that the infrared collection mirror 312 was placed off the optical axis by about 30 degrees. No significant aberrational defects were observed.

A room temperature, triglycine sulfate (TGS) detector (D*=2×10$^9$ cm H$^{1/2}$ W$^{-1}$) and KBr beamsplitter were employed in the Fourier transform-spectrometer 314. All spectra were acquired with 4 cm$^{-1}$ resolution at a mirror velocity of 0.32 cm/s. A triangular apodization function was used with 1X zero filling and, due to the discrete line nature of the emission spectra, phase correction was not applied. Instead, the single-beam power spectra were calculated and plotted, and none of the spectra in FIG. 17, FIG. 18 and FIG. 19 have been corrected for instrumental response.

Figure 17:
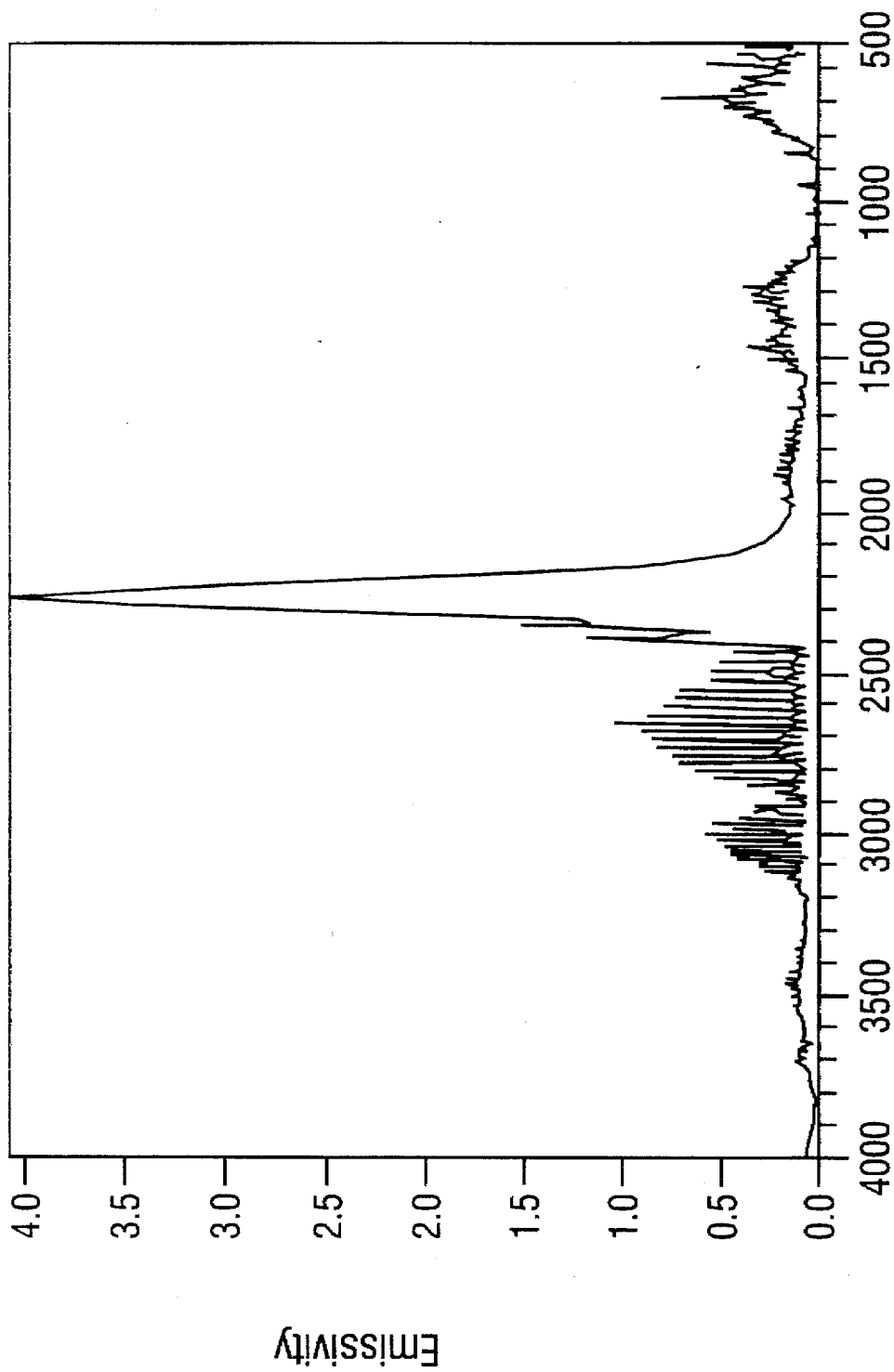
FIG. 17 is a flame infrared emission spectrum of carbon tetrachloride.
Figure 18:
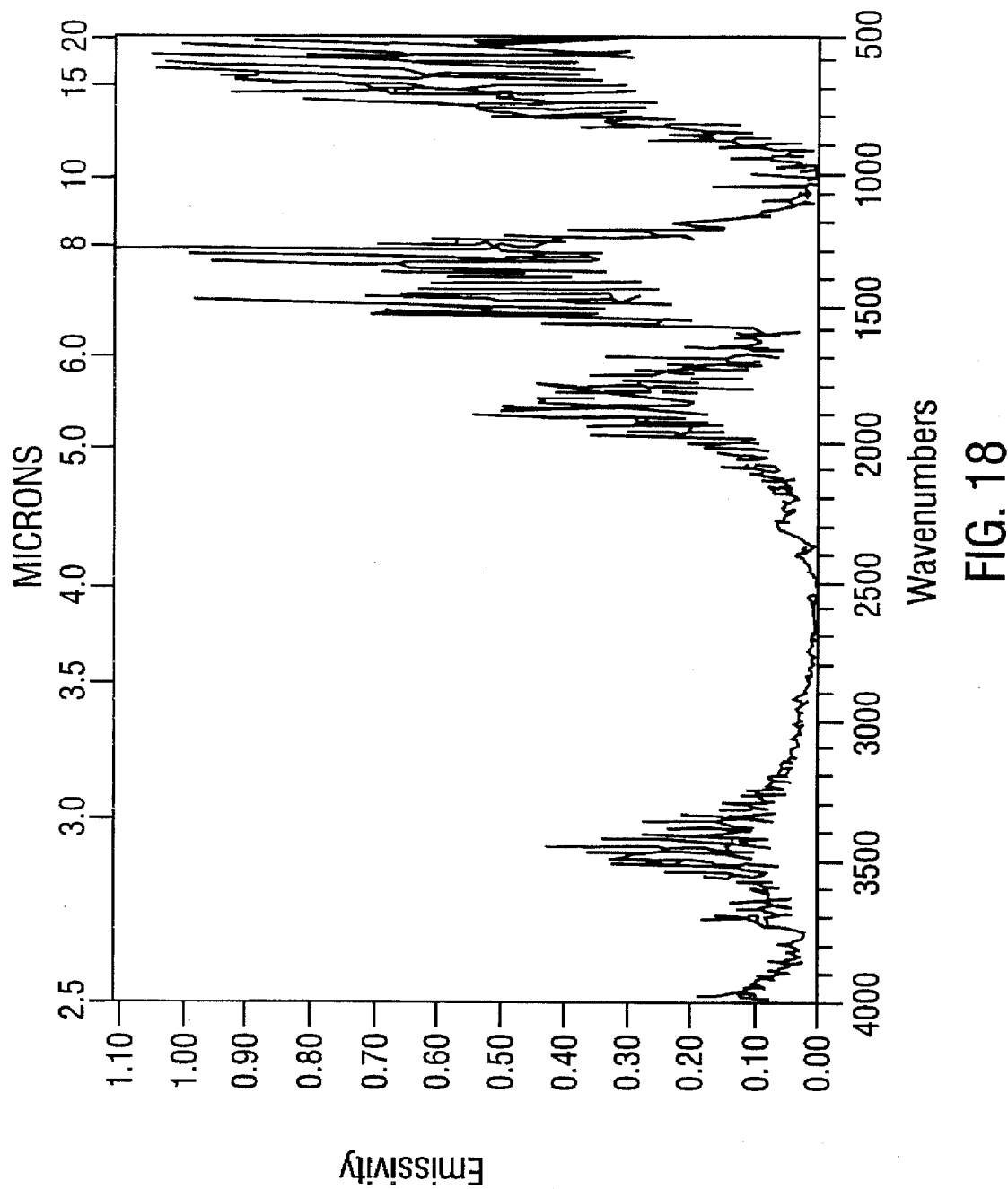
FIG. 18 is a flame infrared emission spectrum of $H_2$/air background at high gain.
Figure 19:
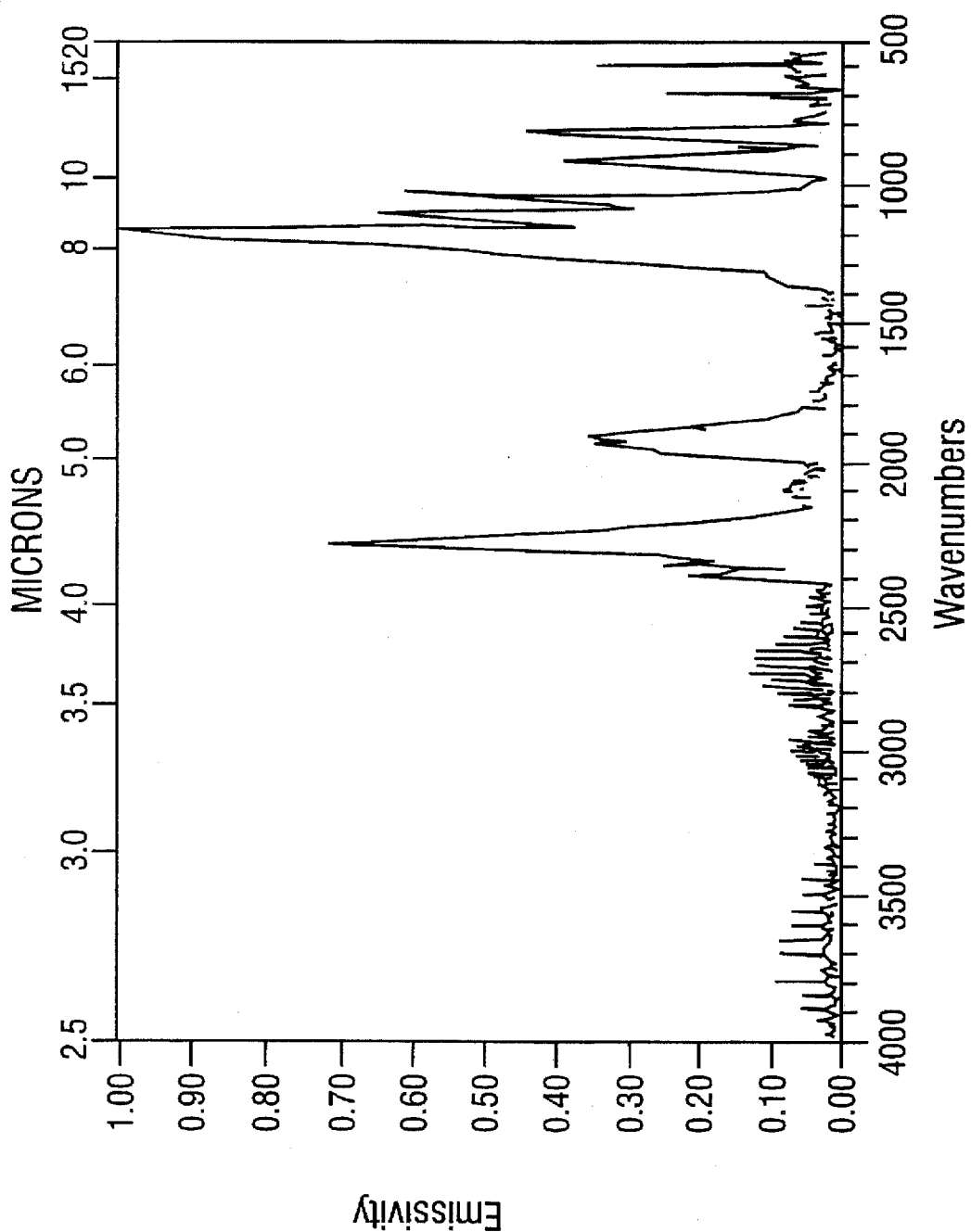
FIG. 19 is a flame infrared emission spectrum of trichlorotrifluoroethane.

FIG. 17 through FIG. 19 are characteristic infrared emission spectra for carbon tetrachloride, the H$_2$/Air flame background and trichlorotrifluoroethane. These spectra clearly show that HCl bands may be observed in the infrared emissions of chlorine containing compounds. They demonstrate that high resolution spectra can, in principle, be obtained from the infrared emission produced by combustion flames.

In the above examples, chorine content was determined by measuring the infrared emissions of vibrationally excited HCl. However, it is understood that the present invention may also be practiced by measuring infrared emissions of other forms of chlorine that may be known to those skilled in the art, including other chlorine containing compounds and forms of chloride isotopes. This can be done using any method known to those skilled in the art that is capable of measuring these other forms of chlorine.

Although the invention has been described by reference to preferred embodiments, it is not intended that the novel methods, compositions and apparatus be limited thereby but various modifications are intended to be included as falling within the spirit and broad scope of the foregoing example and the following claims.

REFERENCES

The following references are incorporated in pertinent part by reference herein for the reasons cited above.

U.S. Pat. No. 5,473,162.
U.S. Pat. No. 3,836,255.
U.S. Pat. No. 3,516,745.
U.S. Pat. No. 3,749,495.
Belz, H. H. et al., "Continuous-Wave $CO_2$ Laser-Excited Infrared Emission Spectroscopy," *Applied Spectroscopy*, 41: 1009–1019, 1987.
Bernard, B. B., "A Summary of TOG Developments", O. I. Corporation College Station, Tex., 1985.
Boyd, R. W., *Radiometry and the Detection of Optical Radiation*; John Wiley: New York, Chapter 10, 1983.
Busch, K. W. et al., *Anal. Chem.* 46:1231, 1974.
Busch, K. W. et al., "Flame/Furnace Infrared Emission Spectroscopy: New Ways of Playing with ID-FIRE," *Spectroscopy*, 4(8):22–36, 1989.
Busch, K. W. et al, "A High-Efficiency Light Collection System for Energy-Limited Infrared Emission Radiometers," *Applied Spectroscopy* 45:964–968, 1991.
Busch, M. A. & Busch, K. W., "Flame Infrared Emission (ID-FIRE): A Versatile, New Element-Specific Detector for Gas Chromatography," *American Laboratory*, 23(11):18–24, 1991a.
Busch, M. A. & Busch, K. W., "A Signal-to-Noise Comparison of Flame/Furnace Infrared Emission (ID-FIRE) Spectrometry with Room Temperature, Non-Dispersive Infrared Absorption Spectrophotometry," *Applied Spectroscopy*, 47:912–921, 1993.
Busch, M. A. & Busch, K. W., "Analytical Applications of Flame/Furnace Infrared Emission Spectrometry," *Spectrochimica Acta Reviews*, 14:303–336, 1991b.
Busch, M. A. & Busch, K. W., "Signal-to-Noise Considerations in Flame/Furnace Infrared Emission Spectroscopy," *Applied Spectroscopy*, 45:546–554, 1991c.
Christensen, C. P., "Pulsed Transverse Electrodeless Discharge Excitation of a $CO_2$ Laser," *App. Phys. Lett.*, 34(3):211–213, 1979.
Curcio, J. A., Buttrey, D. V. E.; *Appl. Opt.*, 5:231, 1966.
Encyclopedia of Analytical Science, "Isotope Dilution Analysis," 4:2399–2415, 1995.
*Encyclopedia of Science and Technology*, Volume 9, 7th Edition, McGraw-Hill, New York, pp 454–456.
Garrett, R. L., *J. Pet. Tech.*, p. 860, June, 1978.
Gaydon, A. G., *The Spectroscopy of Flames*; Chapman and Hall: London, pp. 221–243, 1974.
Gaydon, A. G., Wolfhard, H. G., *Flames, Their Structure, Radiation and Temperature*, 4th ed.; Chapman and Hall: London, pp. 238–259, 1979.
*Handbook of Chemistry and Physics*, CRC Press, Boca Raton, Fla., 72nd ed., Section 3, pp. 191, 519 and 520, 1991.
*Handbook of Chemistry and Physics*, CRC Press, Boca Raton, Fla., 72nd ed., Section 3, pp. 273, 321 and 363, 1991.
Herzberg, Gerhard, "Spectra of Diatomic Molecules," *Molecular Spectra and Molecular Structure*, Van Nostrand, Vol. 1, 1950.
Hudson, M. K. & Busch, K. W., "Infrared Emission from a Flame as the Basis for Chromatographic Detection of Organic Compounds," *Analytical Chemistry*, 59:2603–2609, 1987.
Hudson, M. K. & Busch, K. W., "Flame Infrared Emission Detector for Gas Chromatography," *Analytical Chemistry*, 60:2110–2115, 1988.
Jurgensen, H. and Winefordner, J. D., "Use of Active Nitrogen in Analytical Chemiluminescence Spectroscopy," *Talanta*, 31:777–782, 1984.
Karger, B. L. et al., *An Introduction to Separation Science*, Wiley, N.Y., pp. 232–236, 1973.
Kishman, J. et al, "The Dielectric Discharge as an Efficient Generator of Active Nitrogen for Chemiluminescence and Analysis," *Applied Spectroscopy*, 37:545–552, 1983.
Kubala, S. W. et al., "Determination of Total Inorganic Carbon in Aqueous Samples with a Flame Infrared Emission Detector," *Analytical Chemistry*, 61:1841–1846, 1989a.
Kubala, S. W. et al., "Determination of Chloride and Available Chlorine in Aqueous Samples by Flame Infrared Emission," *Analytical Chemistry*, 61:2785–2791, 1989b.
Kubala, S. W. et al., "Design and Performance of a Direct-Reading, Multichannel Spectrometer for the Determination of Chlorinated Purgeable Organic Compounds by Flame Infrared Emission Spectroscopy," *Talanta*, 38:589–602, 1991.
Lam, K. Y. et al., "Design and Performance of a New Continuous Flow Sample-Introduction System for Flame Infrared—Emission Spectrometry: Applications in Process Analysis, Flow Injection Analysis, and Ion-Exchange High-Performance Liquid Chromatography," *Talanta*, 40:867–878, 1993.
Lam, C. K. Y. et al., "An Investigation of the Signal Obtained from a Flame Infrared Emission (ID-FIRE) Detector," *Applied Spectroscopy*, 44:318–325, 1990.
Manahan, S. E., *Environmental Chemistry*, 3rd. Ed., Willard Grant Press: Boston, Mass. 1979.
Mavrodineanu and Boiteux, "Flame Spectroscopy," 1965, Wiley, N.Y.
McNair, H. M., Bonelli, E. J., *Basic Gas Chromatography*, 5th ed., Varian Instrument Division, Palo Alto, Calif., pp. 81–5, 1969.
Nakamoto, K., *Infrared Spectra of Inorganic and Coordination Compounds*; John Wiley: New York, p. 77, 1963.
Plyler, E. K., *J. Res. Nat. Bur. Stand*, 40:113, 1948.
Putley, E. H. In: *Optical and Infrared Detectors*, Keyes, R. J., Ed.; Springer-Verlag: Berlin, Chapter 3, 1980.
Ravishankar, S. et al., "An Element-Specific, Dual-Channel, Flame Infrared Emission, Gas Chromatography Detector for Chlorinated and Fluorinated Hydrocarbons," *Applied Spectroscopy*, 44: 1247–1258, 1990a.
Ravishankar, S. et al., "Dual-Channel Flame Infrared Emission Detector for Gas Chromatography," *Analytical Chemistry*, 62:1604–1610, 1990b.
Ravishankar, S. et al., "Spatial Emission Characteristics of a Capillary-Burner Excitation Source for a Flame Infrared Emission (FIRE) Radiometer," *Applied Spectroscopy*, 45:1684–1694, 1991.
Skoog, D. A., "Principles of Instrumental Analysis," 3rd Ed., p. 297, Saunders College Publishing, 1985.
Small, R. A. et al., *International Laboratory*, May, 1986.
*Standard Methods for the Examination of Water and Wastewater*, Greenburg, A. E., Trussel, R. R., Clesceri, L.

S., Franson, M. A. H., Eds., American Public Health Association, 16th Ed., Washington, D.C. pp. 286–294, 1985.

Tilotta, D. C. et al., "A Miniature Electrical Furnace as an Excitation Source for Low-Temperature, Gas-Phase, Infrared Emission Spectroscopy," *Applied Spectroscopy*, 45:178–185, 1991.

Tilotta, D. C. et al., "Evaluation of Thermospray and Cross-Flow Pneumatic Nebulization as a Means of Interfacing a Flame Infrared Emission (FIRE) Radiometer to a High-Performance Liquid Chromatograph," *Applied Spectroscopy*, 47:192–200, 1993.

Tilotta, D. C. et al., "Fourier-Transform Flame Infrared Emission Spectroscopy," *Applied Spectroscopy*, 43:704–709, 1989.

Whitlock, W. H. et al., *Microcontamination*, May, 1988.

Zhang, Y. et al., "Pre-excitation, Catalytic Oxidation of Analytes over Hopcalite in Flame/Furnace Infrared Emission (FIRE) Spectrometry," *Applied Spectroscopy*, 46:631–639, 1992a.

Zhang, Y. et al., "Evaluation of an Improved Burner Design for a Flame Infrared Emission (FIRE) Gas Chromatography Detector," *Applied Spectroscopy*, 46:930–939, 1992b.

Zhang, Y. et al., "Terminal and Intermediate Combustion Products Observed from 2.0–5.0 mm in Flame/Furnace Infrared Emission Spectrometry," *Applied Spectroscopy*, 46:1673–1684, 1992c.

What is claimed is:

1. A method of quantitatively determining chlorine content of a first sample, the method comprising: combining said first sample with a second sample containing chlorine isotopically enriched with either a $^{35}Cl$ or $^{37}Cl$ isotope to form a mixture; and exciting said mixture such that the mixture emits an infrared spectrum, and wherein the chlorine content of the first sample is quantitatively determined from the infrared emissions of the mixture.

2. A method of quantitatively determining chlorine content of a sample, comprising the steps of:

(A) mixing a first sample containing an unknown content of chlorine in its naturally occurring isotopic form with a second sample containing a known content of chlorine isotopically enriched with a chosen chlorine isotope, so as to form a mixture;

(B) converting at least a portion of the chlorine in said mixture to vibrationally excited HCl, said HCl emitting a ro-vibrational infrared spectrum; and (C) measuring infrared emissions from said vibrationally excited HCl;

wherein the chlorine content of the first sample is quantitatively determined by comparing the HCl infrared emissions of the chosen chlorine isotope with the HCl infrared emissions of the other chlorine isotope present in said vibrationally excited HCl.

3. A method useful for quantitatively determining the chloride ion content of a solution, comprising the steps of:

(A) mixing a first aqueous sample containing an unknown content of chloride ion in its naturally occurring isotopic form with a second aqueous sample containing a known content of chloride ion isotopically enriched with a chosen chlorine isotope, so as to form a mixture of chloride ions;

(B) subjecting said mixture of chloride ions to electrolysis under conditions effective to convert at least a portion of the chloride ions to $Cl_2$;

(C) reacting said $Cl_2$ with hydrogen under conditions effective to convert at least a portion to HCl;

(D) heating said HCl to convert at least a portion to a vibrationally excited state, said HCl emitting a ro-vibrational infrared spectrum; and (E) measuring infrared emissions from said vibrationally excited HCl;

wherein the chloride ion content of the first sample is quantitatively determined by comparing the HCl infrared emissions of the chosen chlorine isotope with the HCl infrared emissions of the other chlorine isotope present in said vibrationally excited HCl.

4. The method of claim 2 or 3, wherein the chosen chlorine isotope is either $^{35}Cl$ or $^{37}Cl$.

5. The method of claim 4, wherein the chosen isotope comprises between about 90% and about 100% $^{35}Cl$, or between about 90% and about 100% $^{37}Cl$ as a percentage of total Cl present in the isotopically enriched second sample.

6. The method of claim 5, wherein said second sample comprises about 500 mg of isotopically enriched NaCl dissolved in about 25.00 mL of deionized water, said isotopically enriched NaCl containing about 95% $^{37}Cl$ as the chosen chlorine isotope.

7. The method of claim 2, wherein said excited HCl is formed by causing at least a portion of the chlorine of the mixture to be swept into a flame in the presence of hydrogen, and at a temperature sufficient to cause a portion of the HCl present to exist in a vibrationally excited state and to emit a ro-vibrational spectrum.

8. The method of claim 3, wherein said excited HCl molecules are formed by causing at least a portion of the $Cl_2$ to be swept into a flame in the presence of hydrogen, and at a temperature sufficient to cause a portion of the HCl present to exist in a vibrationally excited state and to emit a ro-vibrational infrared spectrum.

9. The method of claim 7 or 8, wherein said flame is a hydrogen/air or hydrogen/oxygen flame.

10. The method of claim 9, wherein the temperature of the flame is at least about 600K.

11. The method of claim 10, wherein the temperature of the flame is about 1200K.

12. The method of claim 2 or 3, wherein the HCl infrared emissions are determined using a Fourier-transform infrared spectrometer.

13. The method of claim 12, wherein said spectrometer collects spectral data from between about 3100–2400 $cm^{-1}$.

14. The method of claim 13, wherein said spectrometer collects spectral data from about 50 spectral scans of the HCl spectrum.

15. The method of claim 13, wherein sufficient volumes of the first sample and the second sample are used so that more than about 50 spectral scans of the HCl spectrum can be accumulated using an FTIR spectrometer.

16. The method of claim 2 or 3, wherein several different mixtures of the first sample and the second sample are analyzed, and wherein the results of said analyses are averaged.

17. The method of claim 2 or 3, wherein a single mixture of the first sample and the second sample is analyzed using a number of rotational lines from the HCl spectrum, and wherein the results of said analyses are averaged.

18. The method of claim 2, wherein the first sample comprises a material selected from process gas, electronic-grade gas, gaseous effluent, air conditioning waste gas and dry cleaning effluent or mixtures thereof.

19. The method of claim 3, wherein the first sample comprises a material selected from industrial process water, aqueous bleach samples, cooling water, sewage treatment effluent, industrial process effluent, drinking water, ground water, surface water or mixtures thereof.

20. The method of claim 3, wherein the first sample comprises a material selected from well water, brine water from wells, aquifer water, outcrop water, spring water, ocean or sea water, lake water, pond water, stream water, creek water, storm water runoff or mixtures thereof.

21. The method of claim 3 wherein the chloride ion content present in the first sample is quantitatively determined based on the ratio of the HCl infrared emissions of the other chlorine isotope to the HCl infrared emissions of the chosen chlorine isotope.

22. The method of claim 21 wherein chloride ion content present in the first sample is quantitatively determined as a concentration based on the HCl infrared emissions of the other chlorine isotope and the HCl infrared emissions of the chosen chlorine isotope using the following equation:

$$Cs = \frac{(Csp)(Vsp)}{Vs} \times \frac{Asp - [(Rm)(Bsp)]}{[(Rm)(Bs)] - As}$$

where:
Cs=concentration of chloride ion in the first sample
Csp=known concentration of chloride ion in the second sample
Vsp=volume of the second sample mixed with the first sample
Vs=volume of the first sample mixed with the second sample
Rs=natural abundance ratio of the chosen chlorine isotope to the other chlorine isotope in the first sample
As=natural abundance fraction of the chosen chlorine isotope in the first sample
Bs=natural abundance fraction of the other chlorine isotope in the first sample
Asp=fraction of the chosen chlorine isotope in the second sample
Bsp=fraction of the other chlorine isotope in the second sample
Rm=measured ratio of the chosen chlorine isotope to the other chlorine isotope determined from the HCl infrared spectrum of the mixture of the first and second solutions.

23. An apparatus useful for quantitatively determining fractional abundance of chlorine isotopes or chloride ion content in a solution using flame infrared spectrometry, comprising:

(A) sample introduction means for converting chloride ions into $Cl_2$ having an electrolysis cell for containing aqueous solutions of NaCl;

(B) sample excitation means having a burner, wherein $Cl_2$ gas from the sample introduction means issues from the burner in the presence of hydrogen and mixes with air or oxygen so as to fuel a flame, thereby combusting a portion of the hydrogen and $Cl_2$ gases so as to generate vibrationally excited HCl molecules, said HCl molecules emitting infrared radiation at a characteristic wavelength;

(C) infrared discriminating detector means having an interferometer and capable of detecting and distinguishing infrared radiation at the characteristic wavelengths of $H^{35}Cl$ and $H^{37}Cl$ and generating an output signal representative thereof; and (D) computation means capable of performing signal processing on the output signal generated by the discriminating detector means so as to provide an output indicative of the relative quantities of $H^{35}Cl$ and $H^{37}Cl$ present in the HCl.

24. The apparatus of claim 23, wherein the burner has two concentric tubes, said tubes constructed to allow air or oxygen to issue from the outer tube and a mixture of hydrogen gas and chlorine gas from the sample introduction means to issue from the inner tube, wherein the hydrogen and chlorine gases issuing from the inner tube mix with the air or oxygen issuing from the outer tube.

25. The apparatus of claim 23, wherein the burner comprises at least one tube, said tube constructed to allow hydrogen gas and chlorine gas from the sample introduction means to issue from said tube in the presence of entrained air.

26. The apparatus of claim 23, wherein the electrolysis cell includes an inlet through which the cell is capable of being purged with a gas containing hydrogen.

27. The apparatus of claim 26, wherein the electrolysis cell is capable of being purged with a gas containing hydrogen using a porous gas frit extending below the working level of the aqueous NaCl solution.

28. The apparatus of claim 23, wherein the electrolysis cell includes at least two electrodes, said electrodes being connected to an electrical power supply so as to cause the generation of $Cl_2$ from aqueous NaCl solutions.

29. The apparatus of claim 28, wherein the electrolysis cell includes two platinum electrodes.

30. The apparatus of claim 23, wherein the electrolysis cell is sealed from the atmosphere.

31. The apparatus of claim 23, wherein the electrolysis cell includes an outlet connected to a conduit through which gases can be liberated from the electrolysis cell and transferred to the sample excitation means.

32. The apparatus of claim 23, wherein the computation means is capable of providing an output indicative of the quantity of $H^{35}Cl$ and $H^{37}Cl$ present in the HCl by performing a Fourier-transform analysis on an output signal from the interferometer to thereby obtain a spectral analysis characteristic of the HCl present.

33. The apparatus of claim 23, wherein the interferometer has a resolution of at least about 0.75 $cm^{-1}$.

34. The apparatus of claim 23, further comprising an exhaust means for removing gases from the area of the excitation means.

35. The apparatus of claim 23, further comprising a blackbody source and moveable mirror; wherein said blackbody source is capable of initiating the infrared discriminating detector means; and wherein said moveable mirror is capable of being deployed into the light-path between the sample excitation means and the infrared discriminating detector means to direct the radiation from said blackbody source to the infrared discriminating detector means; and wherein said moveable mirror is further capable of being removed from the light-path between the sample excitation means and the infrared discriminating detector means.

36. A method useful for quantitatively determining fractional abundance of chlorine isotopes present in a sample, comprising the steps of:

(A) exciting at least a portion of the sample, said portion of the sample emitting a distinctive and characteristic infrared spectra; and (B) measuring infrared emissions from said excited portion of the sample;

wherein the fractional abundance of chlorine isotopes present in the sample is quantitatively determined from the infrared emissions of the portion of the sample.

37. The method of claim 36, wherein the chlorine is converted to vibrationally excited HCl, said HCl emitting a ro-vibrational infrared spectrum; and wherein the infrared emissions from said vibrationally excited HCl is measured.

38. The method of claim 37, wherein the chlorine of the sample is composed of $^{37}Cl$ and $^{35}Cl$.

* * * * *